(12) United States Patent
Urwin et al.

(10) Patent No.: US 12,299,772 B2
(45) Date of Patent: May 13, 2025

(54) WOUND TREATMENT MANAGEMENT USING AUGMENTED REALITY OVERLAY

(71) Applicant: T.J.Smith and Nephew, Limited, Hull (GB)

(72) Inventors: Charlotte Rose Urwin, Hull (GB); Johannes Dagevos van Rij, Skidby (GB)

(73) Assignee: T.J.Smith and Nephew, Limited, Hull (GB)

( * ) Notice: Subject to any disclaimer, the term of this patent is extended or adjusted under 35 U.S.C. 154(b) by 224 days.

(21) Appl. No.: 17/919,369

(22) PCT Filed: Apr. 21, 2021

(86) PCT No.: PCT/EP2021/060312
§ 371 (c)(1),
(2) Date: Oct. 17, 2022

(87) PCT Pub. No.: WO2021/214099
PCT Pub. Date: Oct. 28, 2021

(65) Prior Publication Data
US 2023/0177740 A1    Jun. 8, 2023

(30) Foreign Application Priority Data

Apr. 21, 2020  (GB) ..................................... 2005783
Apr. 21, 2020  (GB) ..................................... 2005788

(51) Int. Cl.
*G06T 11/00*      (2006.01)
*A61B 5/00*       (2006.01)
(Continued)

(52) U.S. Cl.
CPC .............. *G06T 11/00* (2013.01); *A61B 5/445* (2013.01); *A61B 5/743* (2013.01); *A61F 13/36* (2013.01);
(Continued)

(58) Field of Classification Search
CPC . G06T 11/00; G06T 2200/24; G06T 2210/41; G06T 19/006; A61B 5/445;
(Continued)

(56) References Cited

U.S. PATENT DOCUMENTS 3,896,802 A   7/1975  Williams
4,334,530 A   6/1982  Hassell
(Continued)

FOREIGN PATENT DOCUMENTS

CA    3072006 A1 *  2/2019  ........... A61B 5/0531
CN    105232229 A    1/2016
(Continued)

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).
(Continued)

*Primary Examiner* — Jitesh Patel
(74) *Attorney, Agent, or Firm* — Knobbe, Martens, Olson & Bear, LLP

(57) ABSTRACT

At least a method is disclosed for visualizing sensor data from a sensor monitoring a wound. The method can include: receiving senor data generated by one or more sensors monitoring a wound of a patient, the wound being covered with a wound dressing; generating a graphical representation from the sensor data; and presenting the graphical representation to a user via augmented reality so that the graphical representation is overlaid on an area proximate to the patient from a viewing perspective of the user.

21 Claims, 11 Drawing Sheets

(51) Int. Cl.
*A61F 13/36* (2006.01)
*A61B 90/00* (2016.01)
*A61F 13/84* (2006.01)

(52) U.S. Cl.
CPC . *A61B 2090/365* (2016.02); *A61F 2013/8473* (2013.01); *G06T 2200/24* (2013.01); *G06T 2210/41* (2013.01)

(58) Field of Classification Search
CPC ... A61B 5/743; A61B 2090/365; A61F 13/36; A61F 2013/8473
See application file for complete search history.

(56) References Cited

U.S. PATENT DOCUMENTS

| | | |
|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,480,641 B2 | 7/2013 | Jacobs |
| 8,525,340 B2 | 9/2013 | Eckhardt et al. |
| 8,579,872 B2 | 11/2013 | Coulthard et al. |
| 8,644,911 B1 | 2/2014 | Panasyuk et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,204,806 B2 | 12/2015 | Stivoric et al. |
| 9,220,455 B2 | 12/2015 | Sarrafzadeh et al. |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,380,698 B1 | 6/2016 | Li et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,844,145 B2 | 12/2017 | Hsu |
| 9,907,103 B2 | 2/2018 | Chen et al. |
| 9,910,958 B2 * | 3/2018 | Mielekamp ............ A61B 6/463 |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,166,387 B2 | 1/2019 | Bergelin et al. |
| 10,182,740 B2 | 1/2019 | Tonar et al. |
| 10,201,644 B2 | 2/2019 | Haggstrom et al. |
| 10,206,604 B2 | 2/2019 | Bergelin et al. |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,687,984 B2 | 6/2020 | Rovaniemi |
| 10,702,153 B2 | 7/2020 | Shamim et al. |
| 10,716,490 B2 | 7/2020 | Connolly |
| 10,857,038 B2 | 12/2020 | Zamierowski et al. |
| 11,026,847 B2 | 6/2021 | Piotrowski et al. |
| 11,647,922 B2 | 5/2023 | Scherer |
| 11,850,121 B2 | 12/2023 | Rapp |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |

(56) References Cited

U.S. PATENT DOCUMENTS

| | | |
|---|---|---|
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0209896 A1 | 8/2009 | Selevan |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0165717 A1 | 6/2012 | Al Khaburi |
| 2012/0190989 A1 | 7/2012 | Kaiser et al. |
| 2012/0236031 A1* | 9/2012 | Haddick ................ G06F 1/163 345/633 |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0024206 A1* | 1/2013 | Hughes ................ G16Z 99/00 705/3 |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0011892 A1* | 1/2015 | Sostek ................ A61B 5/0077 600/473 |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0053073 A1 | 2/2017 | Allen et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0183705 A1 | 6/2017 | Hicks et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |

(56) References Cited

U.S. PATENT DOCUMENTS

| | | |
|---|---|---|
| 2017/0234802 A1 | 8/2017 | Hicks et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0003579 A1 | 1/2018 | Esposito et al. |
| 2018/0008177 A1 | 1/2018 | Shimuta et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0015028 A1 | 1/2019 | Hicks et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0134280 A1 | 5/2019 | Toth |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0261957 A1 | 8/2019 | Zaslavsky et al. |
| 2019/0290496 A1* | 9/2019 | Brownhill ............... A61F 13/05 |
| 2019/0374387 A1 | 12/2019 | Ribble et al. |
| 2020/0051448 A1* | 2/2020 | Welch .................... G06F 3/016 |
| 2020/0054218 A1 | 2/2020 | Xi |
| 2020/0078482 A1 | 3/2020 | Yoon et al. |
| 2020/0078499 A1 | 3/2020 | Gadde et al. |
| 2020/0100711 A1 | 4/2020 | Choudhury et al. |
| 2020/0147407 A1 | 5/2020 | Efremkin |
| 2020/0214637 A1 | 7/2020 | Brownhill et al. |
| 2020/0281512 A1 | 9/2020 | Grubb et al. |
| 2020/0281513 A1 | 9/2020 | Grubb et al. |
| 2020/0281529 A1* | 9/2020 | Grubb ................ A61B 5/14552 |
| 2020/0289346 A1 | 9/2020 | Hansen et al. |
| 2020/0289347 A1 | 9/2020 | Gowans et al. |
| 2020/0330258 A1 | 10/2020 | Hansen et al. |
| 2020/0360547 A1 | 11/2020 | Smith et al. |
| 2021/0137446 A1 | 5/2021 | Brownhill et al. |
| 2021/0145359 A1 | 5/2021 | Hunt et al. |
| 2021/0212855 A1 | 7/2021 | Hansen et al. |
| 2022/0079509 A1 | 3/2022 | Gellman et al. |
| 2022/0079814 A1 | 3/2022 | Chen et al. |

FOREIGN PATENT DOCUMENTS

| | | | |
|---|---|---|---|
| CN | 105395184 A | | 3/2016 |
| CN | 106102322 A | | 11/2016 |
| CN | 109350362 A | | 2/2019 |
| DE | 102012211015 A1 | | 1/2014 |
| DE | 102013013013 A1 | | 2/2015 |
| EP | 2454990 A2 | | 5/2012 |
| EP | 2565630 A1 | | 3/2013 |
| EP | 3231478 A1 | | 10/2017 |
| EP | 3409190 A1 | | 12/2018 |
| EP | 3499510 A1 | | 6/2019 |
| EP | 3837520 A1 | | 6/2021 |
| EP | 4139904 A1 | | 3/2023 |
| EP | 4157178 A1 | | 4/2023 |
| GB | 2316171 A | | 2/1998 |
| GB | 2563602 A | | 12/2018 |
| JP | 2009225863 A | | 10/2009 |
| KR | 20120119523 A | | 10/2012 |
| KR | 101224629 B1 | | 1/2013 |
| KR | 20140024743 A | | 3/2014 |
| KR | 20140058041 A | | 5/2014 |
| KR | 20160071044 A | | 6/2016 |
| KR | 20190105898 A | | 9/2019 |
| NL | 1027236 C2 | | 4/2006 |
| WO | WO-0021433 A1 | | 4/2000 |
| WO | WO-0043046 A2 | | 7/2000 |
| WO | WO-03067229 A1 | | 8/2003 |
| WO | WO-2006041997 A2 | | 4/2006 |
| WO | WO-2007030379 A2 | | 3/2007 |
| WO | WO-2007072356 A2 | | 6/2007 |
| WO | WO-2008006150 A1 | | 1/2008 |
| WO | WO-2008010604 A1 | | 1/2008 |
| WO | WO-2009052607 A1 | | 4/2009 |
| WO | WO-2009120951 A2 | | 10/2009 |
| WO | WO-2009141777 A1 | | 11/2009 |
| WO | WO-2010020919 A1 | | 2/2010 |
| WO | WO-2010105053 A2 | | 9/2010 |
| WO | WO-2011082420 A1 | | 7/2011 |
| WO | WO-2011113070 A1 | | 9/2011 |
| WO | WO-2011123848 A1 | | 10/2011 |
| WO | WO-2012141999 A1 | | 10/2012 |
| WO | WO-2013026999 A1 | | 2/2013 |
| WO | WO-2013044226 A2 | | 3/2013 |
| WO | WO-2014036577 A1 | | 3/2014 |
| WO | WO-2014116816 A1 | | 7/2014 |
| WO | WO-2015112095 A1 | | 7/2015 |
| WO | WO-2015168720 A1 | | 11/2015 |
| WO | WO-2016025438 A1 | | 2/2016 |
| WO | WO-2016030752 A1 | | 3/2016 |
| WO | WO-2016058032 A1 | | 4/2016 |
| WO | WO-2016073777 A1 | | 5/2016 |
| WO | WO-2016100218 A1 | | 6/2016 |
| WO | WO-2016110564 A1 | | 7/2016 |
| WO | WO-2016187136 A1 | | 11/2016 |
| WO | WO-2016205872 A1 | | 12/2016 |
| WO | WO-2016205881 A1 | | 12/2016 |
| WO | WO-2017021006 A1 | | 2/2017 |
| WO | WO-2017021965 A2 | | 2/2017 |
| WO | WO-2017033058 A1 | | 3/2017 |
| WO | WO-2017037479 A1 | | 3/2017 |
| WO | WO-2017041014 A1 | | 3/2017 |
| WO | WO-2017041385 A1 | | 3/2017 |
| WO | WO-2017041386 A1 | | 3/2017 |
| WO | WO-2017041387 A1 | | 3/2017 |
| WO | WO-2017119996 A1 | | 7/2017 |
| WO | WO-2017205728 A1 | | 11/2017 |
| WO | WO-2017214188 A1 | | 12/2017 |
| WO | WO-2018035612 A1 | | 3/2018 |
| WO | WO-2018060417 A1 | | 4/2018 |
| WO | WO-2018064569 A1 | | 4/2018 |
| WO | WO-2018115461 A1 | | 6/2018 |
| WO | WO-2018144938 A1 | | 8/2018 |
| WO | WO-2018144941 A1 | | 8/2018 |
| WO | WO-2018144943 A1 | | 8/2018 |
| WO | WO-2018144946 A1 | | 8/2018 |
| WO | WO-2018185138 A1 | | 10/2018 |
| WO | WO-2018189265 A1 | | 10/2018 |
| WO | WO-2018209090 A1 | | 11/2018 |
| WO | WO-2018211458 A1 | | 11/2018 |
| WO | WO-2019020550 A2 | | 1/2019 |
| WO | WO-2019020551 A1 | | 1/2019 |
| WO | WO-2019020666 A1 | | 1/2019 |
| WO | WO-2019048624 A1 | | 3/2019 |
| WO | WO-2019048626 A1 | | 3/2019 |
| WO | WO-2019048638 A1 | | 3/2019 |
| WO | WO-2019057651 A1 | | 3/2019 |
| WO | WO-2019063481 A1 | | 4/2019 |
| WO | WO-2019063488 A2 | | 4/2019 |
| WO | WO-2019067264 A1 | | 4/2019 |
| WO | WO-2019072531 A1 | | 4/2019 |
| WO | WO-2019076967 A2 | | 4/2019 |
| WO | WO-2019096828 A1 | | 5/2019 |
| WO | WO-2019140441 A2 | | 7/2019 |
| WO | WO-2019140444 A1 | | 7/2019 |
| WO | WO-2019140448 A1 | | 7/2019 |
| WO | WO-2019140449 A1 | | 7/2019 |
| WO | WO-2019193141 A1 | | 10/2019 |
| WO | WO-2019216883 A1 | | 11/2019 |
| WO | WO-2019230183 A1 | | 12/2019 |
| WO | WO-2019238180 A1 | | 12/2019 |
| WO | WO-2019238181 A1 | | 12/2019 |

(56) References Cited

FOREIGN PATENT DOCUMENTS

| WO | WO-2019238182 A1 | 12/2019 |
| WO | WO-2019238195 A1 | 12/2019 |
| WO | WO-2019238196 A1 | 12/2019 |
| WO | WO-2019238197 A1 | 12/2019 |
| WO | WO-2019238198 A1 | 12/2019 |
| WO | WO-2020002416 A1 | 1/2020 |
| WO | WO-2020043806 A1 | 3/2020 |
| WO | WO-2020139541 A1 | 7/2020 |
| WO | WO-2020157103 A1 | 8/2020 |
| WO | WO-2020159677 A1 | 8/2020 |
| WO | WO-2020167547 A1 | 8/2020 |
| WO | WO-2020242876 A1 | 12/2020 |
| WO | WO-2021059209 A1 | 4/2021 |
| WO | WO-2021250494 A1 | 12/2021 |

OTHER PUBLICATIONS

Bandodkar A.J., et al., "Battery-Free, Skin-Interfaced Microfluidic/Electronic Systems for Simultaneous Electrochemical, Colorimetric and Volumetric Analysis of Sweat," Science Advances, vol. 5 (1), Jan. 18, 2019, retrieved from http://advances.sciencemag.org/content/5/1/eaav3294, 16 pages.

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

George J., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Gonzalez F., et al., "Smart Multi-Level Tool For Remote Patient Monitoring Based On A Wireless Sensor Network and Mobile Augmented Reality," Sensors, vol. 14, Sep. 16, 2014, XP055739337, pp. 17212-17234 (24 pages).

Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

International Search Report and Written Opinion for Application No. PCT/EP2021/060312, mailed on Sep. 7, 2021, 19 pages.

Kiebel T., et al., "Identifying Patients And Visualize Their Vitality Data Through Augmented Reality," Mobile Adhoc and Sensor Systems, Nov. 8, 2010, XP031832088, pp. 757-758 (2 pages).

Klinker K., et al., "Development of a Smart Glass Application for Wound Management," Advances in Databases and Information Systems, Apr. 27, 2019, XP047507766, pp. 157-171.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for µTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mehmood N., et al., "Applications Of Modern Sensors And Wireless Technology In Effective Wound Management: Modern Sensors And Wireless Technology," Journal of Biomedical Materials Research Part B, vol. 102, May 1, 2014, XP055739544, pp. 885-895.

Mostafalu P., et al., "Wireless Flexible Smart Bandage For Continuous Monitoring Of Wound Oxygenation," IEEE Transactions on Biomedical Circuits and Systems, vol. 9 (5), Oct. 1, 2015, XP055526132, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Pang Q., et al., "Smart Flexible Electronics-Integrated Wound Dressing for Real-Time Monitoring and On-Demand Treatment of Infected Wounds," Advanced Science, vol. 7, No. 6, Mar. 2020, 1902673, XP055739532, 10 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Simoska O., et al., "Electrochemical Detection of Multianalyte Biomarkers in Wound Healing Efficacy," ACS Sensors, Nov. 11, 2020, pp. 3547-3557.

"'Smart' Wearable Sensor Developed to Track Healing," retrieved from https://web.archive.org/web/20201203160955/https://www.theengineer.co.uk/smart-wearable-sensor-developed-to-track-healing/, Dec. 3, 2020, 2 pages.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

International Preliminary Report on Patentability for Application No. PCT/EP2021/060312, mailed on Nov. 3, 2022, 12 pages.

\* cited by examiner

WOUND TREATMENT MANAGEMENT USING AUGMENTED REALITY OVERLAY

CROSS-REFERENCE TO RELATED APPLICATIONS

This application is a U.S. national stage application of International Patent Application No. PCT/EP2021/060312, filed Apr. 21, 2021, which claims priority to U.K. Provisional Application Nos. 2005788.1 and 2005783.2 filed on Apr. 21, 2020; the disclosures of which are hereby incorporated by reference in their entirety.

TECHNICAL FIELD

Embodiments described herein relate to apparatuses, systems, and methods for the treatment of wounds, for example using dressings in combination with negative pressure wound therapy.

BACKGROUND

Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound.

SUMMARY

In some aspects, a method is disclosed for visualizing sensor data from a sensor monitoring a wound. The method can include: receiving senor data generated by one or more sensors monitoring a wound of a patient, the wound being covered with a wound dressing; generating a graphical representation from the sensor data; and presenting the graphical representation to a user via augmented reality so that the graphical representation is overlaid on an area proximate to the patient from a viewing perspective of the user.

The method of the preceding paragraph can include one or more of the following features: The method can include determining a location of a marking on or proximate to the wound dressing, and the presenting can include presenting the graphical representation so that the graphical representation is positioned at a set distance from the location from the viewing perspective of the user. The presenting can include presenting the graphical representation so that the graphical representation is positioned above the wound dressing from the viewing perspective of the user. The presenting can include presenting the graphical representation so that the graphical representation is positioned above the wound dressing from the viewing perspective of the user even as the user moves around the patient. The graphical representation can include a color-coding of values of the sensor data. The graphical representation can include a plurality of layers including a first layer representing first variations at the wound detected with a first type of sensor and a second layer representing second variations at the wound detected with a second type of sensor different from the first type of sensor, and the presenting can include presenting the graphical representation so that the first layer and the second layer are separately displayed and overlaid on the area from the viewing perspective of the user. The first layer can be positioned above the second layer from the viewing perspective of the user. The first variations can include temperature variations, and the second variations can include conductivity variations. The graphical representation can include a first side and a second side opposite the first side, and the first side can represent first sensor data detected on one side of the wound dressing and the second side can represent second sensor data detected on another side of the wound dressing opposite the one side of the wound dressing. The presenting can include presenting the graphical representation so that, from the viewing perspective of the user, the first side is positioned above the one side of the wound dressing and the second side is positioned above the another side of the wound dressing. The receiving can be performed in real-time with the presenting. The presenting can include presenting the graphical representation on a head-mounted display. The method can include generating the sensor data by the one or more sensors, and the generating the sensor data can be performed in real-time with the presenting. The one or more sensors can be integrated in the wound dressing. The method can include: presenting a media interface element to the user; and adjusting the graphical representation responsive to a selection of the media interface element by the user. The method can include operating a negative pressure source fluidically connected to the wound dressing to provide negative pressure and deliver a negative pressure wound therapy to the wound.

In some aspects, an apparatus is disclosed for visualizing sensor data from a sensor monitoring a wound. The apparatus can include an input and a controller. The input can receive senor data generated by one or more sensors configured to monitor a wound of a patient. The wound can be covered with a wound dressing. The controller can: generate a graphical representation from the sensor data, and output the graphical representation for presentation to a user via augmented reality so that the graphical representation is overlaid on an area proximate to the patient from a viewing perspective of the user.

The apparatus of the preceding paragraph can include one or more of the following features: The controller can determine a location of a marking on or proximate to the wound dressing, and the controller can output the graphical representation for presentation so that the graphical representation is positioned on a display at a set distance from the location from the viewing perspective of the user. The controller can output the graphical representation for presentation so that the graphical representation is positioned on a display above the wound dressing from the viewing perspective of the user. The controller can output the graphical representation for presentation so that the graphical representation is positioned on a display above the wound dressing from the viewing perspective of the user even as the user moves around the patient. The graphical representation can include a color-coding of values of the sensor data. The graphical representation can include a plurality of layers including a first layer representing first variations at the wound detected with a first type of sensor and a second layer representing second variations at the wound detected with a second type of sensor different from the first type of sensor. The presenting can include presenting the graphical representation so that the first layer and the second layer are separately displayed and overlaid on the area from the viewing perspective of the user. The first layer can be positioned above the second layer from the viewing perspective of the user. The first variations can include temperature variations, and the second variations can include conductivity variations. The graphical representation can include a first side and a second side opposite the first side, and the first side can represent first sensor data detected on one side of the wound dressing and the second side can represent second sensor data detected on another side of the wound dressing opposite the one side of the wound dressing. The controller can output the graphical representation for presentation so that, from the viewing perspective of the user, and the first side can be positioned above the one side of the wound dressing and the second side can be positioned above the another side of the wound dressing. The input can receive the sensor data in real-time with the controller outputting the graphical representation for presentation. The apparatus can include a head-mounted display configured to present the graphical representation. The one or more sensors can generate the sensor data in real-time with the controller outputting the graphical representation for presentation. The one or more sensors can be integrated in the wound dressing. The controller can: output a media interface element for presentation to the user; and adjust the graphical representation responsive to a selection of the media interface element by the user. The apparatus can include a negative pressure source configured to be fluidically connected to the wound dressing to provide negative pressure and deliver a negative pressure wound therapy to the wound.

In some aspects, a method is disclosed for assisting with placement of a wound dressing for treatment of a wound. The method can include: determining a relative position of a wound dressing; generating a movement instruction from the relative position, the movement instruction being usable to guide a manual placement by a user of the wound dressing on a wound of a patient; and presenting the movement instruction to the user via augmented reality so that the movement instruction is overlaid on an area proximate to the patient from a viewing perspective of the user.

The method of the preceding paragraph can include one or more of the following features: The method can include determining a location of a marking on or proximate to the wound, and the presenting can include presenting the movement instruction so that the movement instruction is positioned at a set distance from the location from the viewing perspective of the user. The presenting can include presenting the movement instruction so that the movement instruction is positioned above the wound from the viewing perspective of the user. The presenting can include presenting the movement instruction so that the movement instruction is positioned above the wound from the viewing perspective of the user even as the user moves around the patient. The movement instruction can include an indication of a direction in which to move the wound dressing. The movement instruction can include an indication of a direction in which to move the wound dressing and a distance in which to move the wound dressing. The movement instruction can include an indication to shift and rotate the wound dressing. The determining can include determining the relative position of the wound dressing with respect to the wound or a position on the patient at which another wound dressing was previously placed. The presenting can include presenting the movement instruction on a head-mounted display. The method can include: determining that the wound dressing is positioned on the patient at a first location rather than a second location; generating sensor data by one or more sensors monitoring the wound; and adjusting the sensor data to compensate for the wound dressing being positioned on the patient at the first location rather than the second location. The method can include operating a negative pressure source fluidically connected to the wound dressing to provide negative pressure and to deliver a negative pressure wound therapy to the wound.

In some aspects, an apparatus is disclosed for assisting with placement of a wound dressing for treatment of a wound. The apparatus can include a controller and a memory device. The controller can: determine a relative position of a wound dressing, generate a movement instruction from the relative position, the movement instruction being usable to guide a manual placement by a user of the wound dressing on a wound of a patient, and output the movement instruction for presentation to the user via augmented reality so that the movement instruction is overlaid on an area proximate to the patient from a viewing perspective of the user. The memory device can store the movement instruction.

The apparatus of the preceding paragraph can include one or more of the following features: The controller can determine a location of a marking on or proximate to the wound, and the controller can output the movement instruction for presentation so that the movement instruction is positioned at a set distance on a display from the location from the viewing perspective of the user. The controller can output the movement instruction for presentation so that the movement instruction is positioned on a display above the wound from the viewing perspective of the user. The controller can output the movement instruction for presentation so that the movement instruction is positioned on a display above the wound from the viewing perspective of the user even as the user moves around the patient. The movement instruction can include an indication of a direction in which to move the wound dressing. The movement instruction can include an indication of a direction in which to move the wound dressing and a distance in which to move the wound dressing. The movement instruction can include an indication to shift and rotate the wound dressing. The controller can determine the relative position of the wound dressing with respect to the wound or a position on the patient at which another wound dressing was previously placed. The apparatus can include a head-mounted display configured to present the movement instruction. The controller can: determine that the wound dressing is positioned on the patient at a first location rather than a second location; and adjust sensor data generated by one or more sensors monitoring the wound to compensate for the wound dressing being positioned on the patient at the first location rather than the second location. The apparatus can include a negative pressure source configured to be fluidically connected to the wound dressing to provide negative pressure and deliver a negative pressure wound therapy to the wound.

BRIEF DESCRIPTION OF THE DRAWINGS

Embodiments of the present disclosure will now be described hereinafter, by way of example only, with reference to the accompanying drawings in which.

DETAILED DESCRIPTION

Introduction

Figure 1:
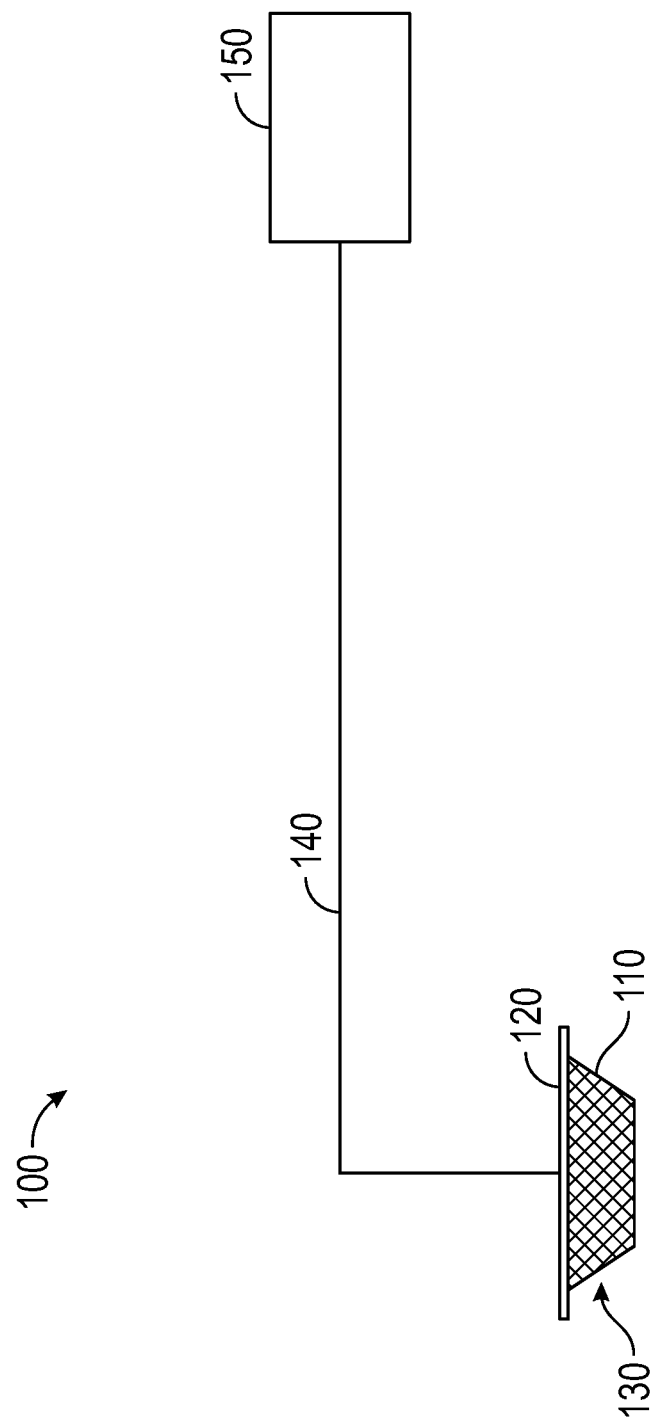
FIG. 1 illustrates a wound therapy system.

Consistency of care can be important when treating a wound that is difficult to heal. For example, the consistency of dressing change intervals for treating a wound may influence how quickly the wound heals.

The ability of a healthcare provider to triage a wound may traditionally be limited to a visual inspection of the wound and its neighboring area between dressing changes. However, features disclosed herein can desirably, in certain implementations, enable to the healthcare provider to visualize and understand characteristics of the wound and its neighboring area through a visual inspection of the wound dressing or its neighboring area and without removing a wound dressing covering the wound. This can allow the healthcare provider to assess the wound through an accustomed visual review of an area around the wound regardless of whether the wound dressing may be covering the wound.

Information about the wound can, in accordance with features disclosed herein, be presented at a point of care (POC) as a graphical representation of data detected from or determined about the wound or its neighboring area. The data can be detected or determined from one or more sensors (for instance, one or more accelerometers, gyroscopes, magnetometers, impedance or conductivity sensors, perfusion sensors, thermistors, pH sensors, pressure sensors, or optical sensors, among other types of sensors) integrated in a wound dressing or positioned proximate to the wound or the wound dressing. The graphical representation can be depicted as presented or anchored proximate to the wound so that the data may be shown to the healthcare provider in the context of the wound area, which can help leverage the experience of the healthcare provider with assessing the wound by viewing an area near the wound.

The graphical representation can by shown in the form of an augmented reality (AR) overlay on or around the wound dressing, which can be presented by a head-mounted display (HMD), mobile device, a morphological projection technique, or another type of display. The graphical representation may be a heatmap that uses a color-coding of data to visually represent different values of the data. The heatmap can include a number of heatmap levels where each heatmap level may represent a different set of data (for instance, temperature, conductivity, pH, or the like) detected around or determined about the wound or its neighboring area. A relative position or an opacity of the heatmap levels, among other characteristics, can be adjusted by the healthcare provider to facilitate a comparison of different sets of data.

The graphical representation can present the information in real-time or substantially real-time with its detection from or determination about the wound or its neighboring area, and thus the graphical representation can be used to permit the healthcare provider to understand a current environment at the wound. Alternatively, the graphical representation can present the information under control of user-adjustable media interface elements (such as, a play/pause button, a rewind button, a fast forward button, or the like), which can be used to navigate through environments at the wound over time and assist in understanding the information in both a positional context and a temporal context.

The position of the graphical representation can be aligned or fixed with respect to one or more characteristics of or around the wound (for instance, one or more skin spots, one or more periwound features, a shape of the wound, a shape of the wound dressing, a position of the wound dressing, or one or more markings on the wound dressing) from the perspective of the healthcare provider. The one or more characteristics of or around the wound can thus serve as one or more fiducial markers (sometimes referred to as placement markers) to facilitate an accurate positioning of the graphical representation, as well as permit an automatic adjustment to the positioning responsive to changes in a position, a speed, or a distance between two or more of a number of fiducial markers so that the graphical representation may appear anchored from a viewing perspective of the healthcare provider. Because a resolution of the graphical representation may exceed the granularity of the data detected from or determined about the wound, values of the data detected from or determined about the wound may be calculated (for instance, interpolated) to enhance the resolution of the graphical representation or smooth out transitions in the graphical representation.

Features disclosed herein can desirably, in certain implementations, assist the healthcare provider in correctly manually placing the wound dressing or one or more other components in a care environment, as well as to quantify a discrepancy of an incorrect placement of the wound dressing or one or more other components. The wound dressing or the one or more other components can include one or more sensors or one or more fiducial markers, which can be used in combination with an electronic device and potentially one or more other sensors to monitor a position of the wound dressing or the one or more other components. The position of the wound dressing or the one or more other components with the respect to the wound can be used to generate instructions to the user to guide correct movement of the wound dressing or the one or more other components. This can facilitate consistent placement of the wound dressing or the one or more other components to allow for consistent data generation by the wound dressing or the one or more other components or for data generation by inconsistent placement to be post-processed to maintain longitudinal or latitudinal consistency.

Wound Dressing Placement and Wound Monitoring

Some aspects disclosed herein relate to apparatuses and methods for monitoring or treating biological tissue with sensor-enabled substrates. The sensor-enabled technologies disclosed herein are broadly applicable to any type of therapy that may benefit from sensor-enabled substrates and may be utilized for data collection that can be relied upon by healthcare providers to make both diagnostic and patient management decisions.

The data collected by a sensor-enabled substrate can, before or after further processing by a processor, be presented by an augmented reality (AR) display. The information presented by the AR display may be overlaid on an area proximate to the sensor-enabled substrate from a viewing perspective of a healthcare provider so that the information can be understood by the healthcare provider in the context of where the information is sensed or relates.

The AR display can be used to guide manual placement by the healthcare provider of one or more components of a therapy or monitoring system, such as the sensor-enabled substrate. The AR display may, for example, indicate to the healthcare provider to move or reorient the sensor-enabled substrate to ensure a desired placement, such as consistent placement of the sensor-enabled substrate relative to a previous placement of another sensor-enabled substrate over a wound.

Sensors can be mounted on or embedded within substrates configured to be used in the treatment of both intact and damaged human or animal tissue. Such sensors may collect information about the surrounding tissue and transmit such information to a computing device or a caregiver to be utilized in further treatment. The sensors may be attached to the skin anywhere on the body, including areas for monitoring arthritis, temperature, or other areas that may be prone to problems and require monitoring.

The sensor features disclosed herein may be incorporated into treatments for wounds or in a variety of other applications, such as monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Throughout this specification reference is made to a wound. The term wound is to be broadly construed and encompasses open and closed wounds in which skin is torn, cut or punctured or where trauma causes a contusion, or any other superficial or other conditions or imperfections on the skin of a patient or otherwise that benefit from pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk) and provide other benefits.

As used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects pressure that is X mmHg below 760 mmHg or, in other words, a pressure of (760–X) mmHg. In addition, negative pressure that is "less" or "smaller" than X mmHg corresponds to pressure that is closer to atmospheric pressure (for example, –40 mmHg is less than –60 mmHg). Negative pressure that is "more" or "greater" than –X mmHg corresponds to pressure that is further from atmospheric pressure (for example, –80 mmHg is more than –60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

FIG. 1 illustrates a wound therapy system 100 (sometimes referred to as a reduced pressure wound therapy system, a negative pressure wound therapy system, a TNP system, or a wound treatment system) comprising a wound filler 130 placed inside a wound cavity 110, the wound cavity 110 sealed by a wound cover 120. The wound filler 130 in combination with the wound cover 120 may be referred to as a wound dressing. A conduit 140 (such as a single or multi lumen tube) can be connected the wound cover 120 with a wound therapy device 150 (sometimes as a whole or partially referred to as a pump assembly) configured to supply reduced or negative pressure. The wound cover 120 can be in fluidic communication with the wound cavity 110. The wound therapy device 150 can be canisterless (meaning that exudate is collected in the wound dressing or is transferred via the conduit 140 for collection to another location) or include or support a canister.

The wound therapy device 150 can be mounted to or supported by the wound dressing, or adjacent to the wound dressing. The wound filler 130 can be any suitable type, such as hydrophilic or hydrophobic foam, gauze, inflatable bag, and so on. The wound filler 130 can be conformable to the wound cavity 110 such that it substantially fills the wound cavity 110. The wound cover 120 can provide a substantially fluid impermeable seal over the wound cavity 110. In some cases, the wound cover 120 has a top side and a bottom side, and the bottom side adhesively (or in any other suitable manner) seals with the wound cavity 110. The conduit 140 or any other conduit disclosed herein can be formed from polyurethane, PVC, nylon, polyethylene, silicone, or any other suitable material.

The wound cover 120 can have a port (not shown) configured to receive an end of the conduit 140. In some cases, the conduit 140 can otherwise pass through or under the wound cover 120 to supply reduced pressure to the wound cavity 110 so as to maintain a desired level of reduced pressure in the wound cavity 110. The conduit 140 can be any suitable article configured to provide at least a substantially sealed fluid flow pathway or path between the wound therapy device 150 and the wound cover 120, so as to supply the reduced pressure provided by the wound therapy device 150 to wound cavity 110.

The wound cover 120 and the wound filler 130 can be provided as a single article or an integrated single unit. In some cases, no wound filler is provided and the wound cover 120 by itself may be referred to as the wound dressing. The wound dressing may then be connected, via the conduit 140, to a source of negative pressure of the wound therapy device 150. In some cases, though not required, the wound therapy device 150 can be miniaturized and portable, although larger conventional pumps such can also be used.

The wound cover 120 can be located over a wound site to be treated. The wound cover 120 can form a substantially sealed cavity or enclosure over the wound site. The wound cover 120 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate.

The wound therapy device 150 can include a pressure source, such as a source of negative pressure. The wound therapy device 150 can deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even −150 mmHg, can be supplied by the wound therapy device 150. The wound therapy device 150 can provide continuous or intermittent negative pressure therapy.

In operation, the wound filler 130 can be inserted into the wound cavity 110, and wound cover 120 can be placed so as to seal the wound cavity 110. The wound therapy device 150 can provide negative pressure to the wound cover 120, which may be transmitted to the wound cavity 110 via the wound filler 130. Fluid (such as, wound exudate) can be drawn through the conduit 140 and stored in a canister. In some cases, fluid is absorbed by the wound filler 130 or one or more absorbent layers (not shown).

The wound dressing can incorporate a number of electronic components, including one or more sensors or controllers, which can be utilized in order to monitor characteristics of or around the wound cavity 110. The electronic components can transmit, such as wirelessly or via a wired connection, sensor data or processed data to one or more electronic devices, such as to facilitate processing of the sensor data or processed data or visual presentation of information responsive to the sensor data or processed data. Collecting and analyzing data from the wound cavity 110 can provide useful insights towards determining whether a wound is on a healing trajectory, selecting proper therapy, determining whether the wound has healed, or the like.

A number of sensor technologies can be used in or alongside the wound dressing. For example, one or more sensors can be incorporated onto or into a substrate (such substrate can be referred to as a sensor-integrated substrate). The one or more sensors can be provided as an individual material layer that is placed directly or indirectly over or in the wound cavity 110. The substrate can be part of a larger wound dressing apparatus, such as part of a single unit dressing. Additionally or alternatively, the substrate can be placed directly or indirectly over or in the wound cavity 110 and then covered by a secondary wound dressing, which can include one or more of gauze, foam or other wound packing material, a superabsorbent layer, a drape, a fully integrated dressing like the Pico or Allevyn Life dressing manufactured by Smith & Nephew, or the like.

The substrate can be placed in contact with the wound cavity 110 and allow fluid to pass through the substrate while causing little to no damage to the tissue in the wound cavity 110. The substrate can be flexible, elastic, extensible, or stretchable or substantially flexible, elastic, extensible, or stretchable in order to conform to or cover the wound cavity 110.

The substrate can support multiple electronic components and multiple electronic connections interconnecting at least some of the multiple electronic components. The multiple electronic components can be or include one or more sensors, amplifiers, capacitors, resistors, inductors, controllers, or the like. The electronic connections can electrically connect one or more of the electronic components. The electronic connections can be can be tracks printed on the substrate, such as using copper, conductive ink (such as silver ink, graphite ink, etc.), or the like. At least some of the electronic connections can be flexible or stretchable or substantially flexible or stretchable.

The multiple electronic components can be controlled by a control module, which may include a controller and a memory device. The control module can receive and process one or more measurements obtained by the one or more sensors. The control module can include one or more controllers or microprocessors, memory, or the like. The control module can be positioned on, supported by, or proximate to the wound dressing or away from the wound dressing.

The wound dressing or wound dressing components described herein can be part of a kit that also includes the wound therapy device 150. One or more components of the kit, such as the substrate, secondary dressing, or the wound therapy device 150 can be sterile.

Figure 2:
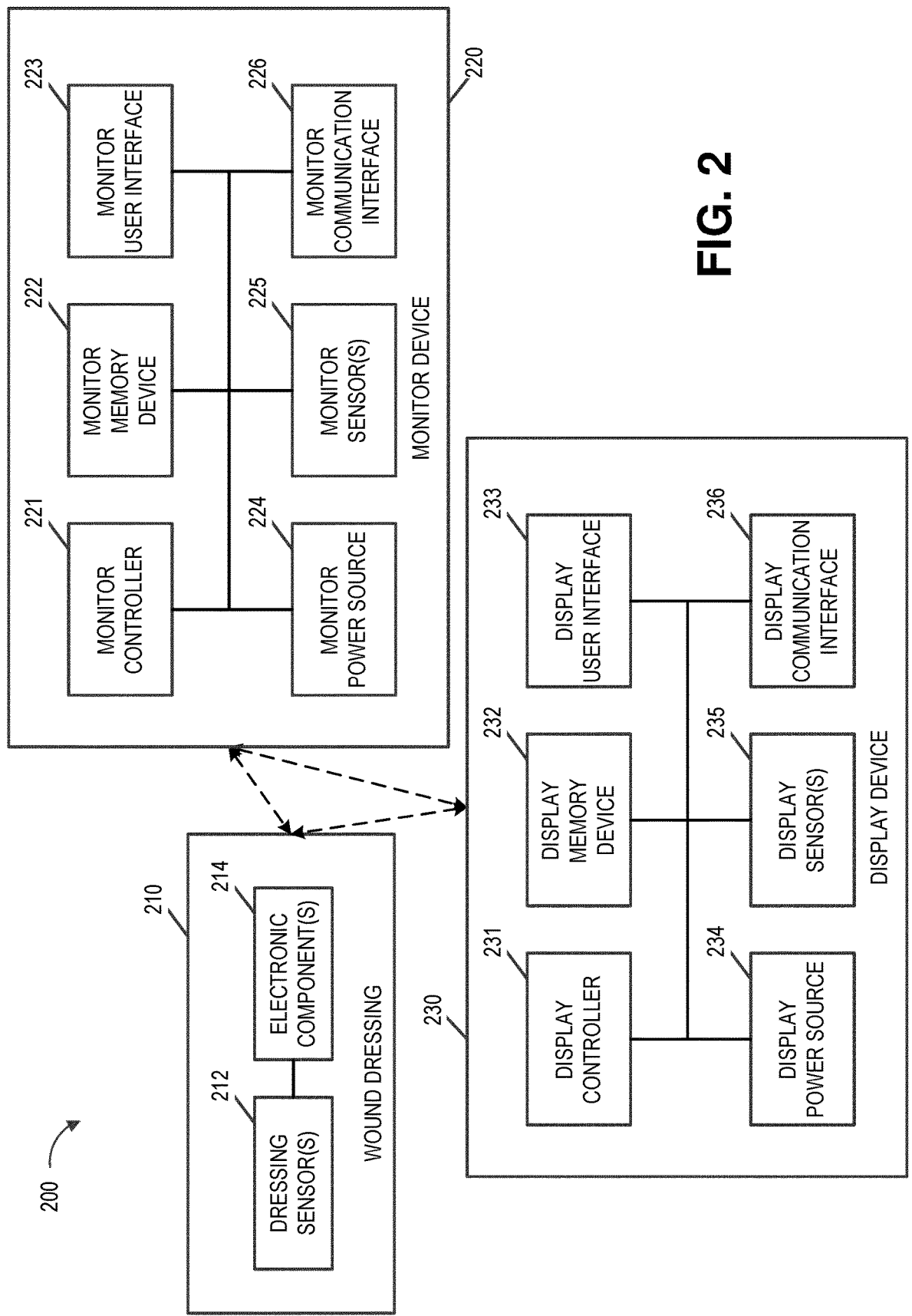
FIG. 2 illustrates a wound dressing, a dressing monitor device, and a display device.

FIG. 2 illustrates a wound monitoring system 200 including a wound dressing 210, a monitor device 220, and a display device 230 in communication with one another. The wound monitoring system 200 can facilitate collection of sensor data from or around a wound covered by the wound dressing 210. The sensor data can, in turn, be passed to the monitor device 220 or the display device 230 for processing, such as for generation of a graphical representation for presentation to a healthcare provider. Although the monitor device 220 and the display device 230 are shown as separate in FIG. 2, the monitor device 220 and the display device 230 can instead be one combined device, supported by a common housing, or share one or more components such that the monitor device 220 or the display device 230 may have a particular component (for instance, a user interface or a sensor) which the other does not.

The wound dressing 210 can be an implementation of the wound dressing of FIG. 1. The wound dressing 210 can include one or more dressing sensors 212 configured to generate sensor data responsive to detected conditions at or near the wound. The one or more dressing sensors 212 can include impedance or conductivity sensors (impedance or conductance measurements can, for instance, be used to identify living and dead tissue, or monitor progress of healing), temperature sensors (temperature measurements can, for instance, be used to provide information about the wound environment or ambient air), optical sensors which may include light sources or light detectors (spectral features of tissue can, for instance, be used to understand tissue health or healing trajectory), pH sensors, pressure sensors, perfusion sensors, accelerometers, gyroscopes, magnetometers, or the like. The wound dressing 210 can include one or more electronic components 214 that can facilitate operation of the one or more dressing sensors 212 (such as through control or provision of power) or communication, such as via radio waves or one or more electrical wires, of the sensor data or dressing data (such as a dressing type or an assigned dressing identifier for uniquely identifying the wound dressing 210 from multiple different wound dressings) to the monitor device 220 or the display device 230.

The wound dressing 210 or one or more other components of the wound monitoring system 200 can include or be used with any of the features described in International Patent Application Publication No. WO2017195038, titled "SENSOR ENABLED WOUND MONITORING AND THERAPY APPARATUS," International Patent Publication No. WO2018189265, titled "COMPONENT STRESS RELIEF FOR SENSOR ENABLED NEGATIVE PRESSURE WOUND THERAPY DRESSINGS," International Patent Publication No. WO2019020551, titled "SKEWING PADS FOR IMPEDANCE MEASUREMENT," and International Patent Publication No. WO2019063488, titled "SENSOR POSITIONING AND OPTICAL SENSING FOR SENSOR ENABLED WOUND THERAPY DRESSINGS AND SYSTEMS," the disclosures of which are incorporated by reference in their entirety.

Although not illustrated, the wound dressing 210 can include a pressure source, such as a source of negative pressure, so that the wound dressing 210 may itself generate negative pressure to provide pressure therapy like the wound therapy device 150 of FIG. 1. An example implementation of a wound dressing with a pressure source is described in International Patent Application Publication No. WO2019193141, titled "NEGATIVE PRESSURE WOUND TREATMENT APPARATUSES AND METHODS WITH INTEGRATED ELECTRONICS," the disclosure of which is incorporated by reference in its entirety.

The monitor device 220 can include a monitor controller 221, a monitor memory device 222, a monitor user interface 223, a monitor power source 224, one or more monitor sensors 225, and a monitor communication interface 226 that may be configured to communicate, such as electrically, with one another. The monitor power source 224 can provide power to one or more components of the monitor device 220 and, for instance, be connected to mains power or include a battery. One or more of the components of the monitor device 220 can be contained in or supported by a monitor device housing. The monitor device 220 can be a hospital patient monitor that may, for example, communicate with one or more other devices in a care environment or via a computer network. Although not illustrated, the monitor device 220 can include a pressure source, such as a source of negative pressure, so that the monitor device 220 may function as a therapy device like the wound therapy device 150 of FIG. 1.

The monitor controller 221 can control operations of one or more other components of the monitor device 220 (for instance, the monitor memory device 222, the monitor user interface 223, the monitor power source 224, the one or more monitor sensors 225, or the monitor communication interface 226) according at least to instructions stored in the monitor memory device 222. The monitor controller 221 can collect the sensor data from the wound dressing 210 via the monitor communication interface 226, process the collected sensor data, generate one or more graphical representations (which can include one or more heatmaps) from the collected or processed sensor data, store the collected or processed sensor data or the one or more graphical representations to the monitor memory device 222, and transmit the collected or processed sensor data or the one or more graphical representations via the monitor communication interface 226. The monitor controller 221 can collect sensor data from the wound dressing 210, the one or more monitor sensors 225, or other sensors in the wound monitoring system 200 and determine a relative position of the wound dressing 210 from the collected sensor data. The monitor controller 221 may use the relative position to generate one or more movement instructions for guiding a manual placement the wound dressing 210 on the wound and transmit the one or more movement instructions via the monitor communication interface 226.

The monitor user interface 223 can include one or more output elements, such as visual feedback devices (for example, light emitting diodes or a display screen), haptic feedback devices, or audio devices (for example, speakers), that provide user outputs to a user, such as a healthcare provider. The one or more output elements can convey status information to the user like whether the monitor device 220 is functioning successfully, collecting the sensor data from the wound dressing 210, or communicating with the wound dressing 210 or the display device 230. The monitor user interface 223 can include one or more input elements, such as buttons, switches, dials, touch pads, microphones, or touch screens, for receiving user inputs for configuring the wound dressing 210, the monitor device 220, or the display device 230.

The one or more monitor sensors 225 can include one or more accelerometers, gyroscopes, magnetometers, impedance sensors, thermistors, pressure sensors, or optical sensors, among other types of sensors. The one or more monitor sensors 225 can be supported by the monitor device housing or may be remote from the monitor device 220 housing yet usable to monitor characteristics of the monitor device 220 or one or more components or individuals nearby the monitor device 220.

The one or more monitor sensors 225 can be used to detect and monitor a position or motion of the wound dressing 210, the monitor device 220, or the display device 230, as well as one or more nearby items or individuals (such as a patient or a healthcare provider). The one or more monitor sensors 225 can additionally or alternatively be used to detect and monitor other conditions at or near the monitor device 220. The conditions at or near the monitor device 220 may be indicative of one or more conditions at or near a wound covered by the wound dressing 210, such as of ambient conditions around the wound. The one or more monitor sensors 225 can output sensor data usable, for example, to determine how to guide movement of the wound dressing 210 for placement on the wound or how to position the one or more graphical representations for viewing by the user.

The monitor communication interface 226 can be used to communicate with other devices, such as via radio waves or wired communication. The communication via radio waves can be performed according to a communication protocol, such as a Bluetooth™ protocol. The monitor communication interface 226 can communicate with other devices and receive and transmit device usage or sensor data (such as [i] the sensor data generated by the one or more dressing sensors 212 before or after processing by the monitor controller 221, [ii] the sensor data indicative of a position or movement of the wound dressing 210, the monitor device 220, or the display device 230, as well as one or more nearby items or individuals, [iii] the one or more movement instructions for moving the wound dressing 210 for placement, [iv] the one or more graphical representations based at least on the sensor data generated by the one or more dressing sensors 212 before or after processing by the monitor controller 221, [v] alarms, or [vi] changes to a monitoring or therapy program performed by the monitor device 220, among other possibilities), as well as commands (such as an activation command to activate the one or more dressing sensors 212 or a request command to cause the wound dressing 210 to provide sensor data). The monitor communication interface 226 may, in some aspects, be unable to communicate farther than 10 meters, 30 meters, or 100 meters with the wound dressing 210 or the display device 230.

The display device 230 can include a display controller 231, a display memory device 232, a display user interface 233, a display power source 234, one or more display sensors 235, and a display communication interface 236 that may be configured to communicate, such as electrically, with one another. The display power source 234 can provide power to one or more components of the display device 230 and, for instance, be connected to mains power or include a battery. One or more of the components of the display device 230 can be contained in or supported by a display device housing. The display device housing can be head-mountable, so the display device 230 may be a head-mounted display (HMD). Alternatively, the display device housing may not be head-mountable, and the display device 230 can, for example, be a mobile device or a smart television or may operate to project an image, such as via a morphological projection technique.

The display controller 231 can control operations of one or more other components of the display device 230 (for instance, the display memory device 232, the display user interface 233, the display power source 234, the one or more display sensors 235, or the display communication interface 236) according at least to instructions stored in the display memory device 232. The display controller 231 can receive, from the monitor device 220 via the display communication interface 236, the one or more movement instructions to guide movement of the wound dressing 210 and output the one or more movement instructions to the display user interface 233 for presentation to the user. The display controller 231 can receive, from the monitor device 220 via the display communication interface 236, the one or more graphical representations, determine from the sensor data from the wound dressing 210 or the collected or processed sensor data from the monitor device 220 how to position the one or more graphical representations on the display user interface 233, and output the one or more graphical representations to the display user interface 233 for presentation to the user. Additionally or alternatively, the display controller 231 can itself determine the one or more movement instructions or the graphical representations from the sensor data from the wound dressing 210 or the collected or processed sensor data from the monitor device 220.

The display user interface 233 can include one or more output elements, such as visual feedback devices (for example, one or more display screens or light emitting diodes), haptic feedback devices, or audio devices (for example, speakers), that provide user outputs to a user. The one or more output elements can convey the one or more movement instructions to the user (such as visually and via augmented reality), as well as status information like whether the display device 230 is functioning successfully, collecting the sensor data from the wound dressing 210 or the collected or processed sensor data from the monitor device 220, or communicating with the wound dressing 210 or the monitor device 220. The display user interface 233 can include one or more input elements, such as buttons, switches, dials, touch pads, microphones, or touch screens, for receiving user inputs for configuring the display device 230.

The one or more display sensors 235 can include one or more accelerometers, gyroscopes, magnetometers, impedance sensors, thermistors, pressure sensors, or optical sensors, among other types of sensors. The one or more display sensors 235 can be supported by the display device housing or may be remote from the display device housing yet usable to monitor characteristics of the display device 230 or one or more components or individuals nearby the display device 230.

The one or more display sensors 235 can be used to detect and monitor a position or motion of the wound dressing 210, the monitor device 220, or the display device 230, as well as one or more nearby items or individuals (such as a patient or a healthcare provider). The one or more display sensors 235 can additionally or alternatively be used to detect and monitor conditions at or near the display device 230. The conditions at or near the display device 230 may be indicative of one or more conditions at or near a wound covered by the wound dressing 210, such as of ambient conditions around the wound. The one or more display sensors 235 can output sensor data usable, for example, to determine how to guide movement of the wound dressing 210 for placement on the wound or how to position the one or more graphical representations on the display user interface 233.

The display communication interface 236 can be used to communicate with other devices, such as via radio waves or wired communication. The communication via radio waves can be performed according to a communication protocol, such as a Bluetooth™ protocol. The display communication interface 236 can, for example, communicate with other devices and transmit device usage or sensor data (such as [i] the sensor data generated by the one or more dressing sensors 212 before or after processing by the monitor controller 221 or the display controller 231, [ii] the sensor data indicative of a position or movement of the wound dressing 210, the monitor device 220, or the display device 230, as well as one or more nearby items or individuals, [iii] the one or more movement instructions for moving the wound dressing 210 for placement, [iv] the one or more graphical representations based at least on the sensor data generated by the one or more dressing sensors 212 before or after processing by the monitor controller 221, [v] one or more indications of how to position the one or more graphical representations on the display user interface 233, [vi] alarms, or [vii] changes to a monitoring or therapy program performed by the monitor device 220 or the display device 230, among other possibilities, as well as commands (such as an activation command to activate the one or more dressing sensors 212 or a request command to cause the wound dressing 210 to provide sensor data). The display communication interface 236 may, in some aspects, be unable to communicate farther than 10 meters, 30 meters, or 100 meters with the wound dressing 210 or the monitor device 220.

Figure 3:
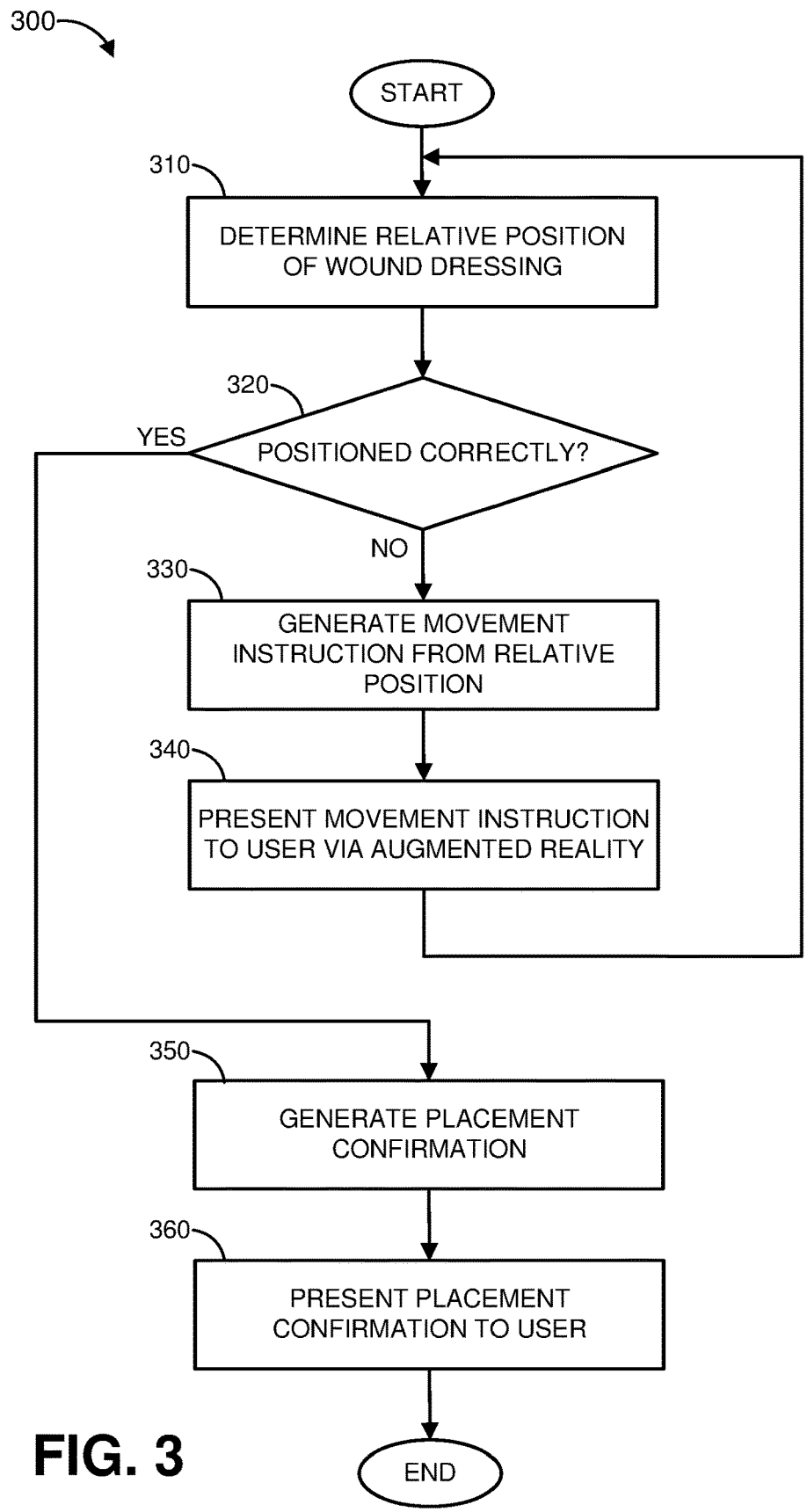
FIG. 3 illustrates a placement guidance process.

FIG. 3 illustrates a positioning guidance process 300. For convenience, the positioning guidance process 300 is described as being performed by the display device 230 and in the context of the wound monitoring system 200, but may instead be implemented in other components or systems described herein, or by other components or systems not shown. The positioning guidance process 300 can advantageously, in certain aspects, assist a healthcare provider by providing dressing placement guidance in augmented reality in the context of a wound area so that the healthcare provider can be supported in accurately placing a wound dressing on a wound. The dressing placement guidance can be easy to understand and follow because the dressing placement guidance may be in the context of the wound area and may even be anchored proximate to the wound.

At block 310, the positioning guidance process 300 can determine a relative position of a wound dressing. For example, the display controller 231 can determine a relative position of the wound dressing 210 with respect to a wound or a position on a patient at which another wound dressing was previously placed. The relative position may be a vector, which can identify an x-axis location, a y-axis location, and a z-axis location for the wound dressing 210 and a magnitude denoting a distance and a direction from the wound dressing 210 to a location, such as a point near the wound or the position on the patient at which the another wound dressing was previously placed. The relative position can be determined from the sensor data (such as data from an accelerometer, gyroscope, magnetometer, or optical sensor) generated by the one or more dressing sensors 212, the one or more monitor sensors 225, or the one or more display sensors 235.

At block 320, the positioning guidance process 300 can determine whether the wound dressing is positioned correctly. For example, the display controller 231 can determine whether the wound dressing 210 may be correctly position by determining if the wound dressing 210 is desirably located and oriented on the patient so that the wound dressing 210 can be used in treatment of the wound. The display controller 231 may have determined or stored a desired location and orientation of the wound dressing 210 on the patient and permitted tolerances for the desired location and orientation. The wound dressing 210 may be correctly placed when the display controller 231 determines that the wound dressing 210 is situated on the patient within the permitted tolerances from the desired location and orientation. The wound dressing 210 may be incorrectly placed when the display controller 231 determines that the wound dressing 210 is not situated on the patient within the permitted tolerances from the desired location and orientation.

If the positioning guidance process 300 determines that the wound dressing is positioned incorrectly, the positioning guidance process 300 can transition to block 330 and can generate a movement instruction from the relative position. For example, the display controller 231 can use the relative position to generate a movement instruction that is usable to guide a manual placement by a user, such as a healthcare provider, of the wound dressing 210 on the wound. The movement instruction can indicate a direction in which to move the wound dressing or a distance in which to move the wound dressing. For instance, the movement instruction can indicate to shift or rotate the wound dressing by a specified amount or degree.

At block 340, the positioning guidance process 300 can present the movement instruction to the user via augmented reality. For example, the display user interface 233 can present the movement instruction in augmented reality on a display, such as a head-mounted display, a screen of a mobile device, or via a morphological projection technique, so that the movement instruction may be overlaid on an area proximate to the patient from a viewing perspective of the user. The movement instruction can be presented with the movement instruction positioned above the wound (or at another location on or above the patient) and appearing to be anchored above the wound (or at the another location) from the viewing perspective so that the location of the movement instruction appears to be fixed with respect to the patient as the user moves around the patient. The display controller 231 may, in some implementations, determine a marking location of a marking on or proximate to the wound or the patient (for instance, one or more skin spots, one or more periwound features, a shape of the wound, a shape of the wound dressing, a position of the wound dressing, or one or more markings on the wound dressing), and the display user interface 233 can present the movement instruction at or at a set distance from the marking location from the viewing perspective.

Subsequent to block 340, the positioning guidance process 300 can return to block 310 and determine a relative position of the wound dressing. The relative position may now be different because the user may have manually moved the wound dressing 210.

If at block 320 the positioning guidance process 300 now determines that the wound dressing is positioned correctly, the positioning guidance process 300 can transition to block 350 and generate a placement confirmation. For example, the display controller 231 can generate a placement confirmation, which can indicate that the wound dressing 210 may be correctly placed and oriented on the patient.

At block 360, the positioning guidance process 300 can present the movement instruction to the user. For example, the display user interface 233 can present the placement confirmation to the user in augmented reality on the display so that the placement instruction may be overlaid on an area proximate to the patient from a viewing perspective of the user. The placement instruction can be presented with the placement instruction positioned above the wound (or at another location on or above the patient) and appearing to be anchored above the wound (or at the another location) from the viewing perspective so that the location of the placement instruction appears to be fixed with respect to the patient as the user moves around the patient.

The positioning guidance process 300 can, in certain implementations, further include adjusting of sensor data gathered by the wound dressing. For example, the monitor controller 221 or the display controller 231 can determine that the wound dressing 210 may have been placed at a different location relative to a previous placement of another wound dressing. Rather than indicating that the different location may be incorrect, the monitor controller 221 or the display controller 231 can determine to adjust and accordingly adjust (for instance, spatially shift or change an orientation of) the sensor data gathered by the one or more dressing sensors 212 to compensate for the placement at the different location.

Although the positioning guidance process 300 may be described in the context of positioning of a wound dressing, the positioning guidance process 300 can be further applied to assisting with placement of other devices on an individual, such as a person or animal. For instance, the positioning guidance process 300 can be used for the placement of an activity monitoring device, such as the activity monitoring devices described in International Patent Application Publication No. WO2019162272, titled "MONITORING OF BODY LOADING AND BODY POSITION FOR THE TREATMENT OF PRESSURE ULCERS OR OTHER INJURIES," International Patent Application Publication No. WO2019234011, titled "DEVICE COMMUNICATION MANAGEMENT IN USER ACTIVITY MONITORING SYSTEMS," and International Patent Application Publication No. WO2019238927, titled "DEVICE HOUSING AND MOUNTING IN USER ACTIVITY MONITORING SYSTEMS," the disclosures of which are incorporated by reference in their entirety.

Figure 4A:
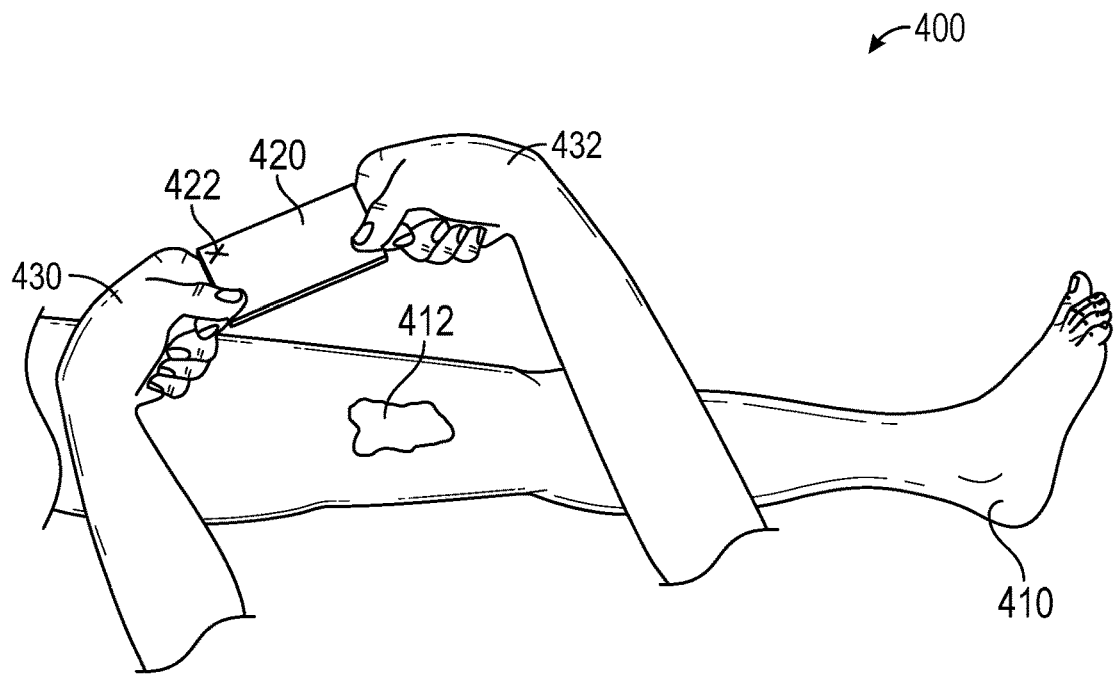
FIGS. 4A-4E illustrate the placement of a wound dressing along with the presentation of guidance instructions to assist with the placement.

FIG. 4A illustrates a wound treatment system 400 prior to activation of movement instructions to assist with placement of a wound dressing 420, such as prior to activation of an overlay on the display user interface 233 of the display device 230 of FIG. 2. The wound treatment system 400 can be shown from a perspective of a user like a healthcare provider. The wound treatment system 400 may be moreover being viewed by the user through a display, such as a head-mounted display.

The wound treatment system 400 can include a limb 410 of a patient that has a wound 412 thereon. The wound treatment system 400 can further include a left hand 430 and a right hand 432 of the user that are holding the wound dressing 420, which can be an implementation of the wound dressing 210 of FIG. 2. The wound dressing 420 can have on its external surface an identification marker 422, which can be used to detect an orientation of the wound dressing 420.

Figure 4B:
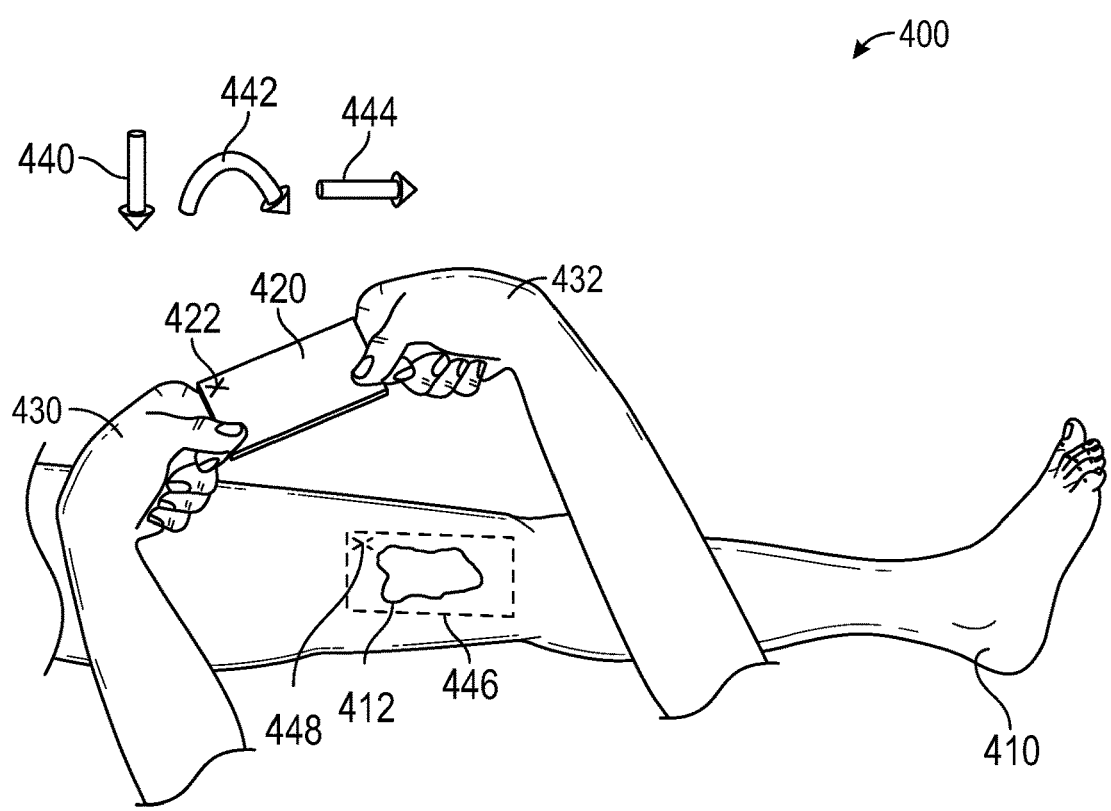

FIG. 4B illustrates the wound treatment system 400 subsequent to activation of the movement instructions, such as subsequent to activation of the overlay on the display user interface 233. The positioning guidance process 300 at block 310, at block 320, at block 330, and at block 340 may have been performed to arrive at the wound treatment system 400 shown in FIG. 4B.

As can be seen in FIG. 4B, the user may now be presented with movement instructions, including a downward arrow 440, a clockwise-orient arrow 442, and a rightward-shift arrow 444. The downward arrow 440, the clockwise-orient arrow 442, and the rightward-shift arrow 444 can respectively indicate to the user to move the wound dressing 420 downward, turn the wound dressing 420 clockwise, and move the wound dressing to the right. A size, color, or one or more other features of the downward arrow 440, the clockwise-orient arrow 442, and the rightward-shift arrow 444 can be used indicate a distance, degree, or amount which the user is instructed to move the wound dressing 420. Moreover, a placement outline 446 and a placement marker 448 can be shown to indicate to the user a desired location and orientation for the wound dressing 420. The user may achieve correct placement of the wound dressing 420 on the limb 410 by lining up the placement outline 446 with the perimeter of the wound dressing 420 and aligning the identification marker 422 with the placement marker 448.

Figure 4C:
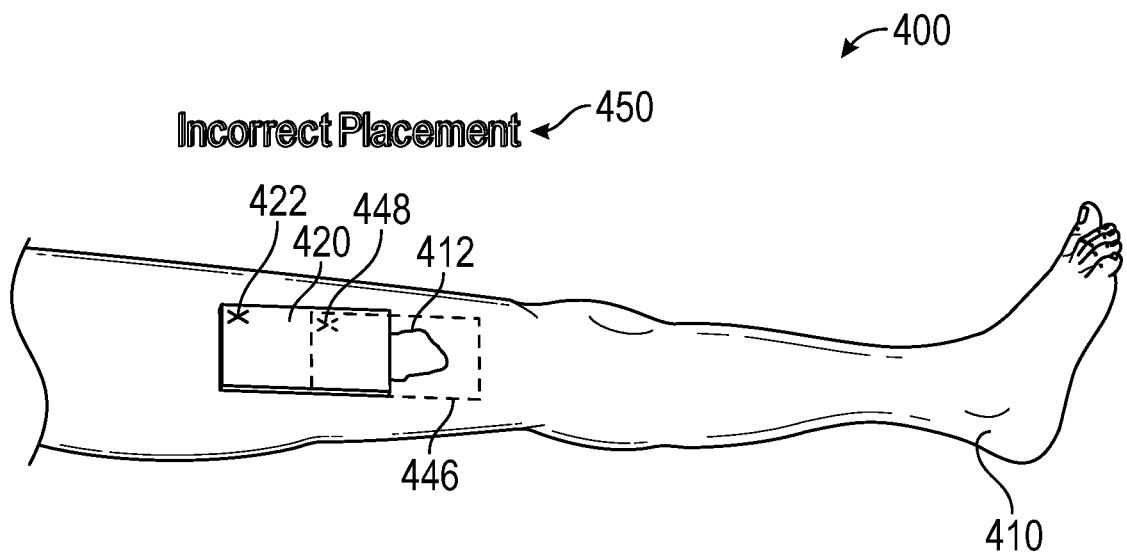

FIG. 4C illustrates the wound treatment system 400 if the wound dressing 420 may be positioned on the limb 410 but not within permitted tolerances from a desired location and orientation. The positioning guidance process 300 at block 310, at block 320, at block 330, and at block 340 may have been performed to arrive at the wound treatment system 400 shown in FIG. 4C. As can be seen in FIG. 4C, an incorrect placement 450 can be presented to the user to indicate that the user should not leave the wound dressing 420 positioned at its current location.

Figure 4D:
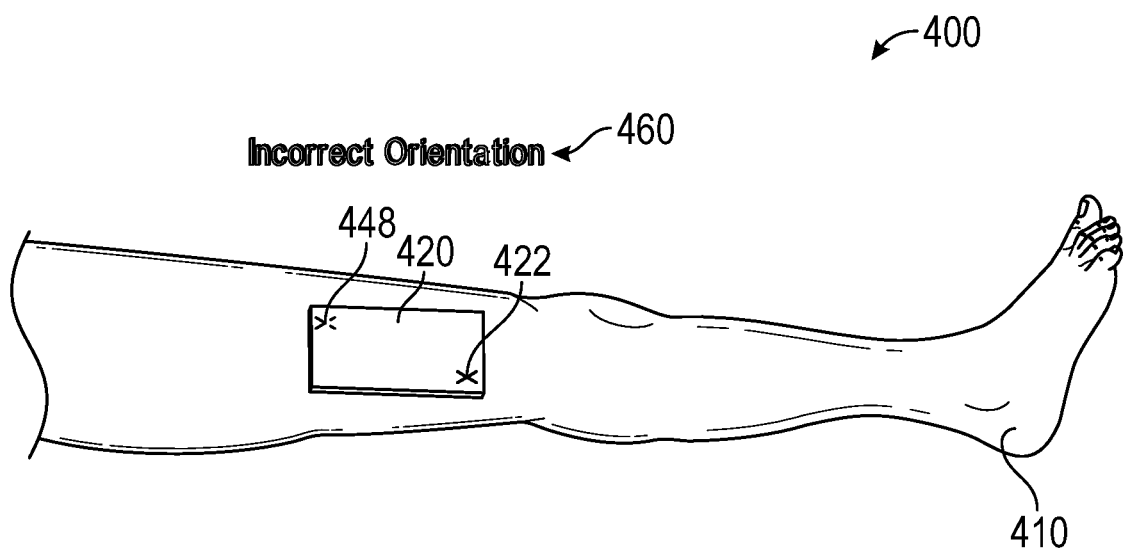

FIG. 4D illustrates the wound treatment system 400 if the wound dressing 420 may be positioned on the limb 410 at a desired location but with an incorrect orientation. The positioning guidance process 300 at block 310, at block 320, at block 330, and at block 340 may have been performed to arrive at the wound treatment system 400 shown in FIG. 4D. As can be seen in FIG. 4D, an incorrect orientation 460 can be presented to the user indicating that the user should not leave the wound dressing 420 positioned at its current orientation.

Figure 4E:
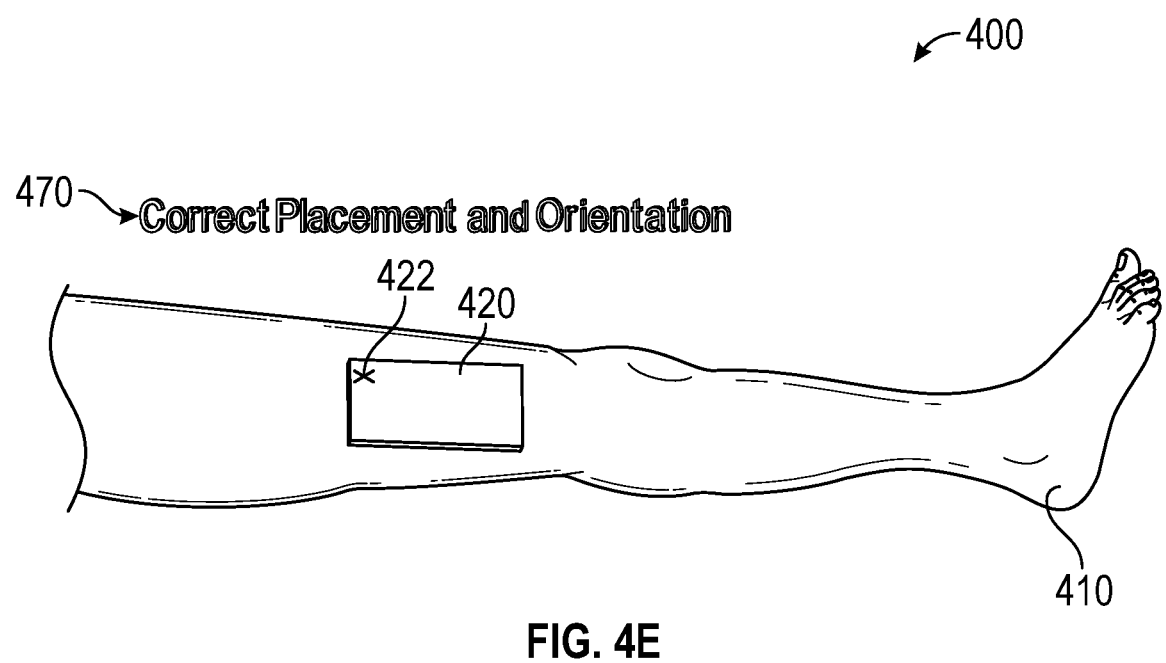

FIG. 4E illustrates the wound treatment system 400 if the wound dressing 420 may be positioned on the limb 410 at a desired location and orientation. The positioning guidance process 300 at block 310, at block 320, at block 350, and at block 360 may have been performed to arrive at the wound treatment system 400 shown in FIG. 4E. As can be seen in FIG. 4E, a correct placement and orientation 470 can be presented to the user indicating that the user should not leave the wound dressing 420 positioned at its current orientation.

In certain implementations, the identification marker 422 may be usable to uniquely identify the wound dressing 420 from multiple different wound dressings. The identification marker 422 may in such implementations be an optical, machine-readable representation of a unique identifier for the wound dressing 420 rather than an X. For example, the identification marker 422 can be used by the monitor device 220 or the display device 230 to uniquely identify the wound dressing 420 from a set of different wound dressings. The monitor device 220 or the display device 230 can, in turn, use identification information determined from the identification marker 422 to automatically customize [i] configurations or settings for communicating with or using the wound dressing 420, [ii] how sensor data from the wound dressing 420 is collected, processed, or associated with a patient record in a database, or [iii] how information is presented to the user in augmented reality (for instance, the identification information can be used to assign default display settings for the wound dressing 420, such as colors, sizes, or which sensor data is assigned to which layers of a graphical representation generated for the wound dressing 420).

Figure 5:
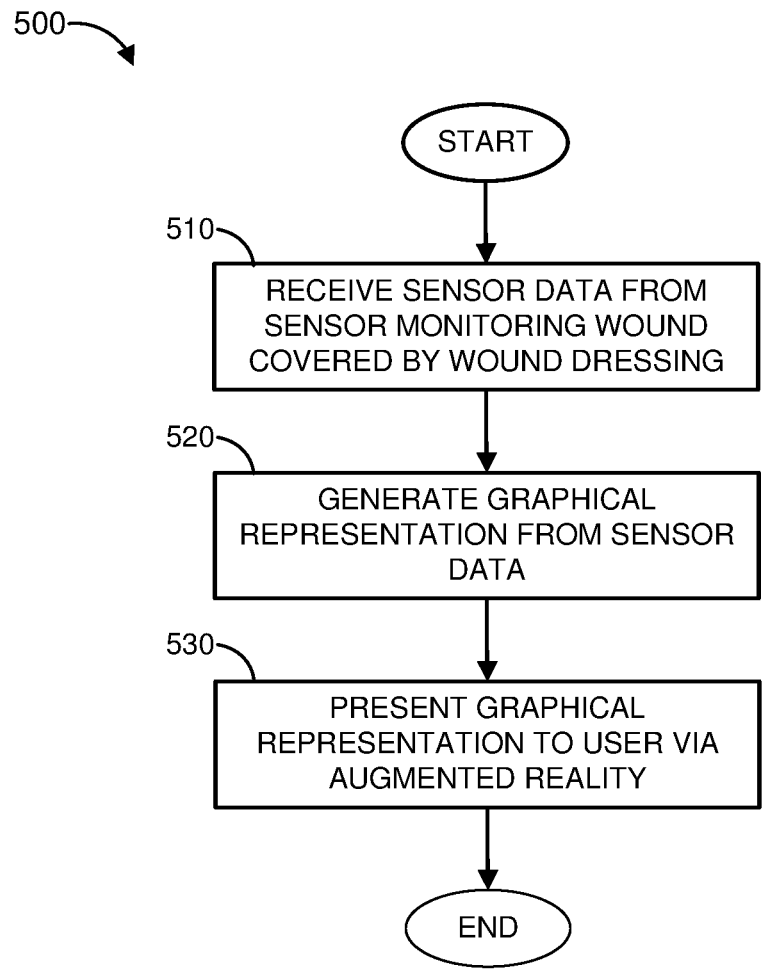
FIG. 5 illustrates a graphical representation generation and presentation process.

FIG. 5 illustrates a graphical representation generation and presentation process 500. For convenience, the graphical representation generation and presentation process 500 is described as being performed by the monitor device 220 and the display device 230 and in the context of the wound monitoring system 200, but may instead be implemented in other components or systems described herein, or by other components or systems not shown. The graphical representation generation and presentation process 500 can advantageously, in certain aspects, assist a healthcare provider by providing sensor-derived information for a wound in augmented reality in the context of a wound area so that the healthcare provider can better understand a condition of the wound without removing the wound dressing. The provided sensor-derived information can be easy to understand and follow because the provided sensor-derived information may be in the context of the wound area and may even be anchored proximate to the wound where corresponding sensor data was detected.

At block 510, the graphical representation generation and presentation process 500 can receive sensor data from a sensor monitoring a wound covered by a wound dressing. For example, the monitor device 220 can receive the sensor data from the wound dressing 210 via the monitor communication interface 226. The sensor data may have been gathered by the one or more dressing sensors 212, which may have been monitoring a wound covered by the wound dressing 210 or its neighboring area. The sensor data may include impedance or conductivity data, temperature data, optical data, pH data, pressure data, perfusion data, accelerometer data, gyroscopic data, or magnetometer data, among other possibilities, for the wound or its neighboring area.

At block 520, the graphical representation generation and presentation process 500 can generate a graphical representation from the sensor data. For example, the monitor device 220 can generate a graphical representation from the sensor data received from the wound dressing 210. The graphical representation can be or include one or more visual representations of variations in one or more characteristics at the wound or its neighboring area, such as how the one or more characteristics vary spatially over the wound or its neighboring area. The graphical representation can include a color-coding of values of the sensor data before or after processing by the monitor controller 221. The graphical representation can have a first side and a second side opposite the first side, and the first side of the graphical representation can represent the sensor data detected on a first side of the wound dressing 210 and the second side of the graphical representation can represent the sensor data detected on a second side of the wound dressing 210 opposite the first side of the wound dressing 210.

The graphical representation can include multiple layers, such as one, two, three, four, or more layers, which may be generated for separate presentation from one another (such as one layer spatially above another layer). The multiple layers can each depict different information, which may be determined from different types sensors of the one or more dressing sensors 212. One of the multiple layers can represent one of impedance or conductivity variations, temperature variations, optical variations, pH variations, pressure variations, perfusion variations, or motion variations, among other possibilities, at the wound or its neighboring area, and another of the multiple layers can represent a different one of the variations at the wound or its neighboring area.

After generation of the graphical representation, the monitor device 220 can transmit the graphical representation to the display device 230 via the monitor communication interface 226.

At block 530, the graphical representation generation and presentation process 500 can present the graphical representation to a user via augmented reality. For example, the display device 230 can present the graphical representation on a display of the display user interface 233, such as a head-mounted display, a screen of a mobile device, or via a morphological projection technique, so that the graphical representation may be overlaid on an area proximate to the patient from a viewing perspective of a user, such as a healthcare provider. The graphical representation can be presented in real-time with receiving the sensor data at block 510, generating the graphical representation at block 520, or generating the senor data by the one or more dressing sensors 212.

The graphical representation can be presented with the graphical representation positioned above the wound (or at another location on or above the patient) and appearing to be anchored above the wound (or at the another location) from the viewing perspective so that the location of the graphical representation appears to be fixed with respect to the patient as the user moves around the patient. The display controller 231 may, in some implementations, determine a marking location of a marking on or proximate to the wound or the patient (for instance, one or more skin spots, one or more periwound features, a shape of the wound, a shape of the wound dressing, a position of the wound dressing, or one or more markings on the wound dressing), and the display user interface 233 can present the graphical representation at or at a set distance from the marking location from the viewing perspective.

Where the graphical representation may have the first side and the second side opposite the first side and the wound dressing 210 may have the first side and the second side opposite the first side, the graphical representation can be presented so that from the viewing perspective the first side of the graphical representation (which can represent the sensor data detected on the first side of the wound dressing 210 before or after processing by the monitor controller 221) may be positioned proximate to the first side of the wound dressing 210, such as overlaid on or above, and the second side of the graphical representation (which can represent the sensor data detected on the second side of the wound dressing 210 before or after processing by the monitor controller 221) may be positioned proximate to the second side of the wound dressing 210, such as overlaid on or above.

Where the graphical representation may include multiple layers, the graphical representation can be presented so that one or more of the multiple layers may be presented separately from one or more other of the multiple layers. For instance, one of the multiple layers can appear to be separated and positioned above another of the multiple layers from the viewing perspective.

Upon completion of the graphical representation generation and presentation process 500, the display user interface 233 can present one or more media interface elements that may permit the user to provide one or more user inputs to control the generation or presentation of the graphical representation. The display user interface 233 may, for example, adjust the presentation of the graphical representation (such as by presenting different types of the sensor data or different timings for the sensor data in the graphical representation or shift locations at which different portions of the graphical representation may be shown) responsive to a user input to the display user interface 233.

Although the graphical representation generation and presentation process 500 may be described using the example of the monitor device 220 and the display device 230 sharing processing responsibilities, the graphical representation generation and presentation process 500 can be performed entirely by the display device 230 in certain implementations.

The graphical representation generation and presentation process 500 may not impact a performance of a negative pressure wound therapy using the wound dressing, such as the wound dressing 210. The wound dressing may continue to cover and seal the wound and maintain negative pressure around the wound while the graphical representation generation and presentation process 500 is performed.

Figure 6A:
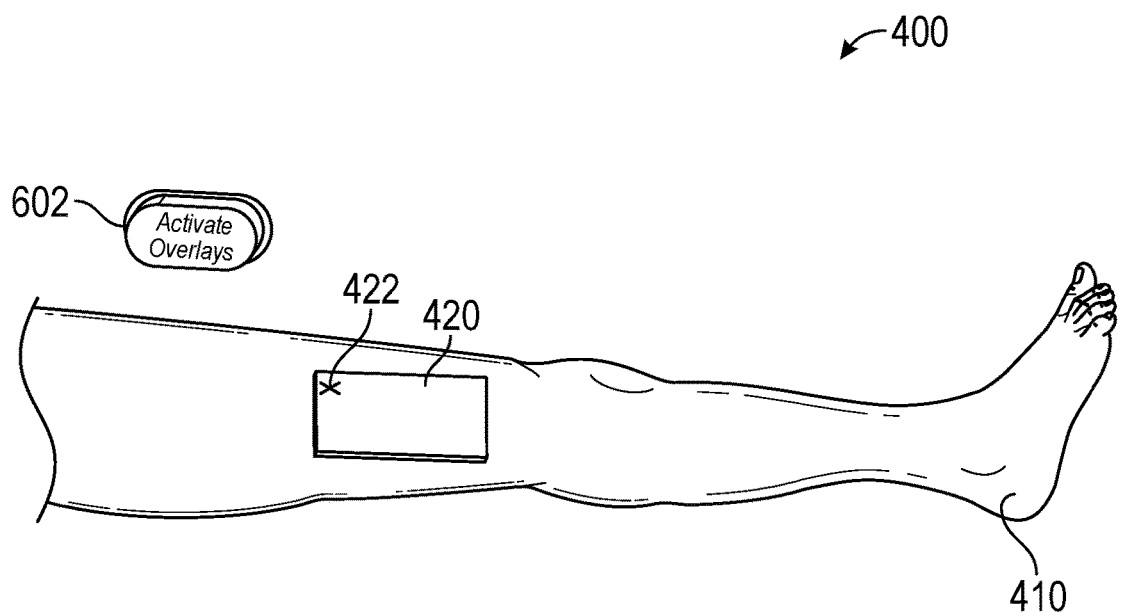
FIGS. 6A-6D illustrate the presentation of a graphical representation of sensor data.

FIG. 6A illustrates the wound treatment system 400 of FIGS. 4A-4E once the wound dressing 420 has been placed at the desired location and orientation. FIG. 6A can, for example, show the wound treatment system 400 after the appearance of the wound treatment system 400 as illustrated in FIG. 4E.

As shown in FIG. 6A, the wound treatment system 400 can include an activate overlays element 602, which may be selectable by the user. The activate overlays element 602 may be presented by the display user interface 233 to the user in augmented reality as shown and detect a selection of the activate overlays element 602 by the user. The selection can be detected, for example, using an optical sensor of the one or more display sensors 235 that detects a gesture by the user toward the activate overlays element 602. The selection of the activate overlays element 602 may initiate the presentation of the graphical representation as described at block 530 of the graphical representation generation and presentation process 500 and trigger the wound treatment system 400 to appear as shown in FIG. 6B.

Figure 6B:
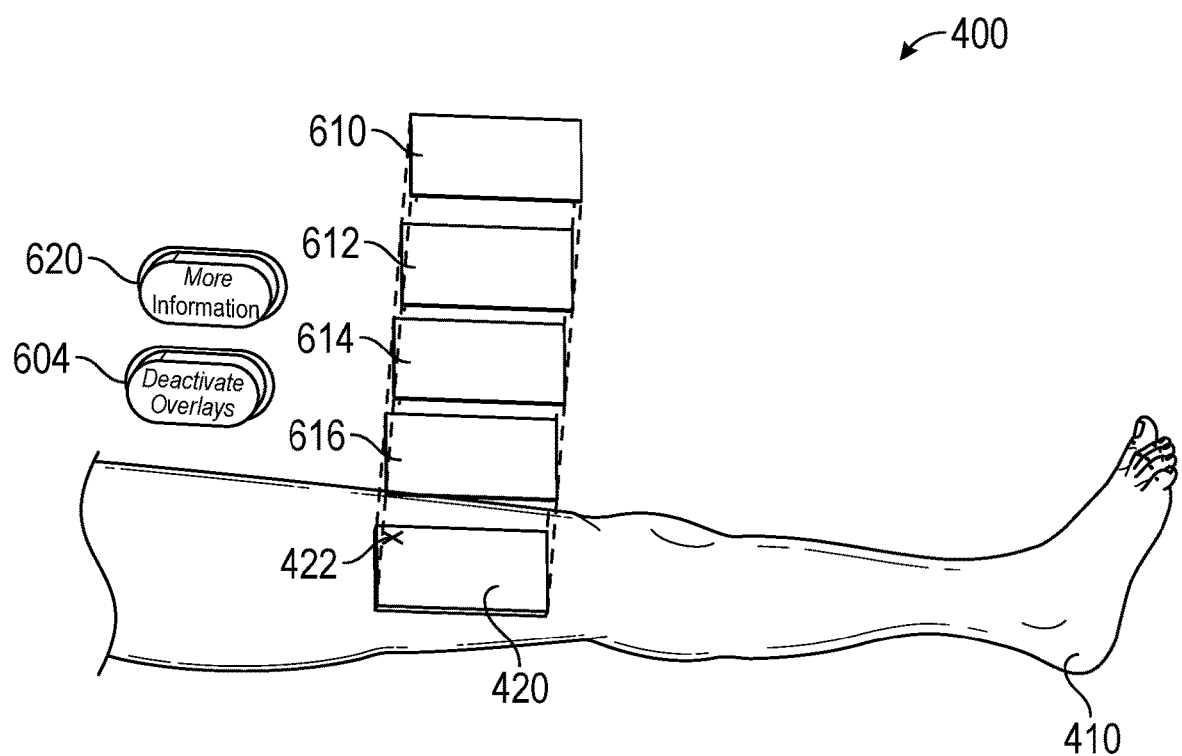

FIG. 6B illustrates the wound treatment system 400 when a graphical representation is presented in augmented reality by the display user interface 233 that includes multiple layers, including a first layer 610, a second layer 612, a third layer 614, and a fourth layer 616. Each of the multiple layers can present different information, which may, for instance, be determined from different types sensors of the one or more dressing sensors 212 monitoring the wound 412. In one example, the first layer 610 may depict impedance or conductivity variations under the wound dressing 420, the second layer 612 may depict temperature variations under the wound dressing 420, the third layer 614 may depict optical variations under the wound dressing 420, and the fourth layer 616 may depict pH variations under the wound dressing 420.

Figure 6C:
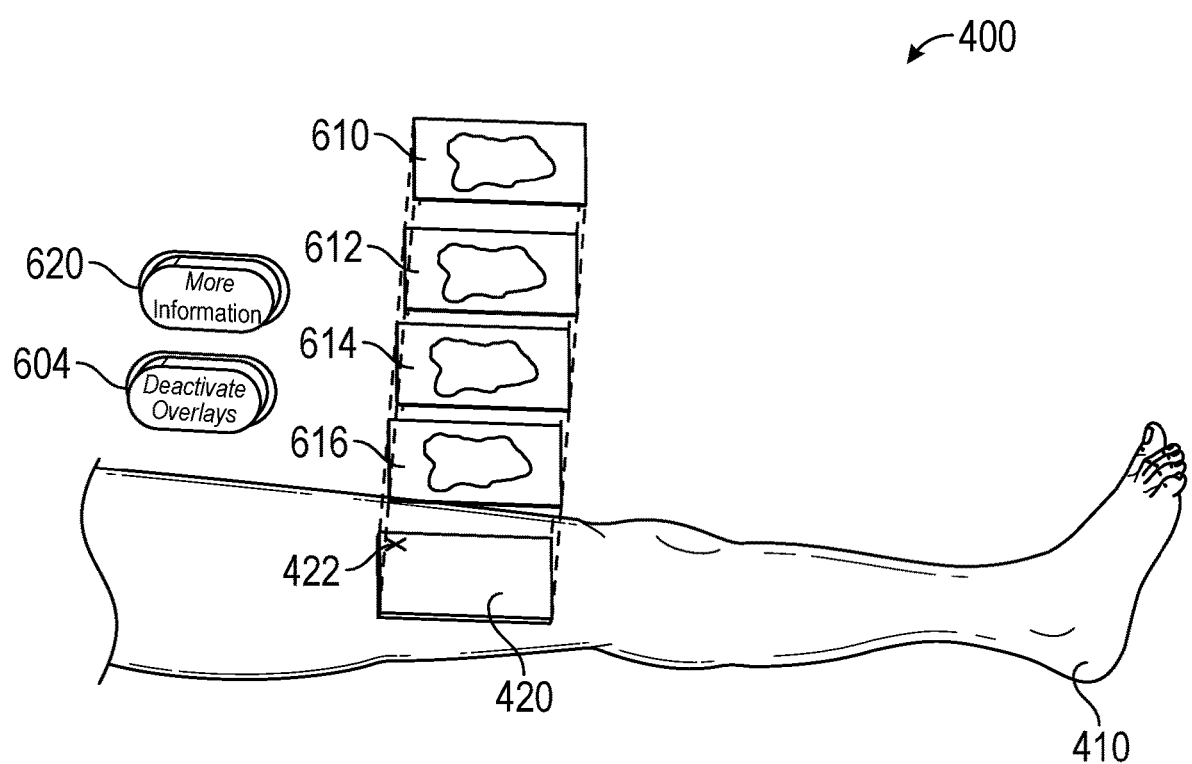

The presentation of information by the multiple layers at a point on each of the multiple layers can, as shown in FIG. 6C, spatially correspond to a characteristic detected under the wound dressing 420 at the point which appears to be directly below the multiple layers from the viewing perspective of the user. As a result, features of the wound 412, such as an outline of the wound 412, can be visible in each of the multiple layers such as shown in FIG. 6C.

A deactivate overlays element 604 and a more information element 620 can be presented in the wound treatment system 400 as illustrated in FIG. 6B. The deactivate overlays element 604 and the more information element 620 can be presented in augmented reality by the display user interface 233, and the display user interface 233 can detect a selection of the deactivate overlays element 604 or the more information element 620 by the user, such as using an optical sensor of the one or more display sensors 235 that detects a gesture by the user toward the deactivate overlays element 604 or the more information element 620. The selection of the deactivate overlays element 604 can deactivate the presentation of the graphical representation and trigger the wound treatment system 400 to appear as shown in FIG. 6A. The selection of the more information element 620 can initiate the presentation of one or more media interface elements and trigger the wound treatment system 400 to appear as shown in FIG. 6D.

Figure 6D:
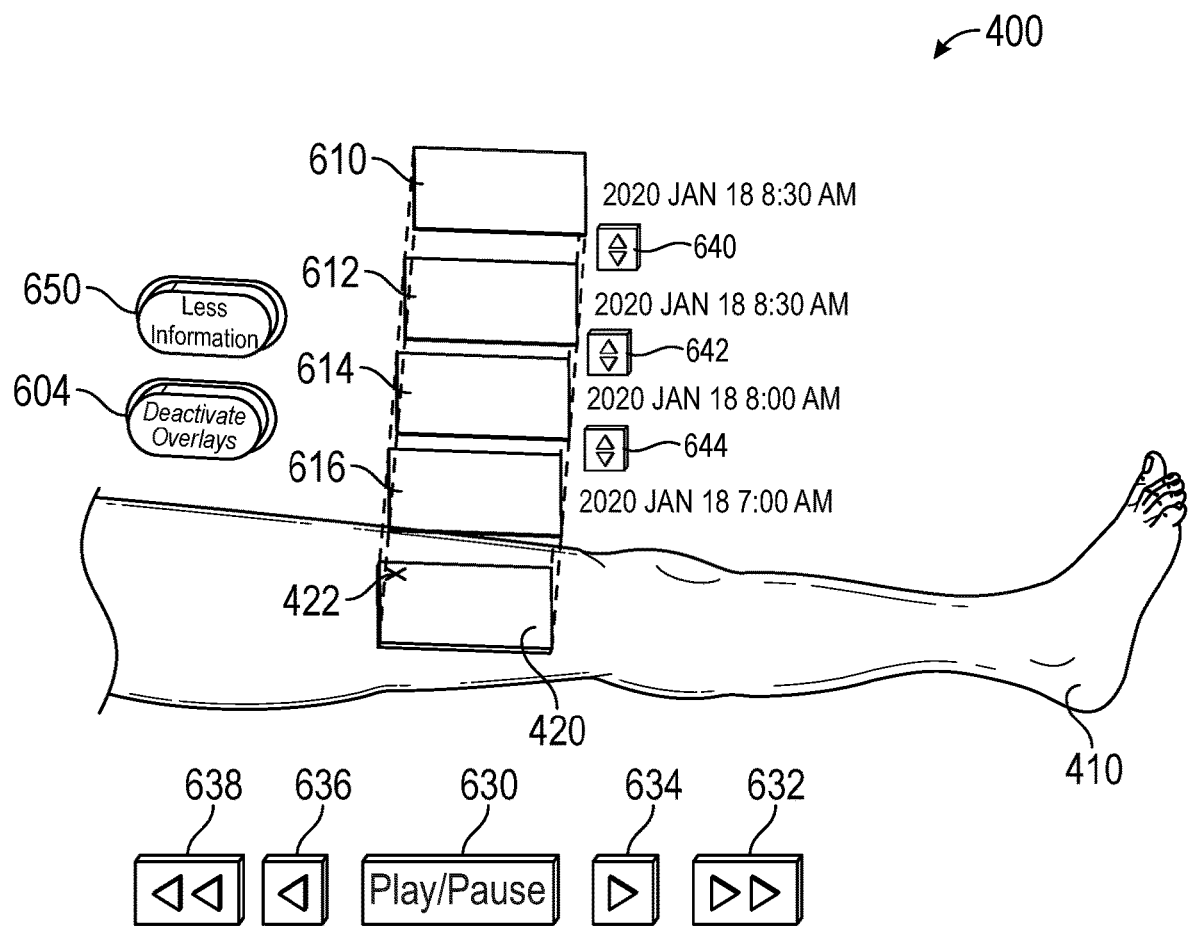

FIG. 6D illustrates the wound treatment system 400 when one or more media interface elements are presented in augmented reality by the display user interface 233. The one or more media interface elements can include a play/pause element 630, a fast forward element 632, a jump forward element 634, a jump reverse element 636, a fast reverse element 638, a first layer switch element 640, a second layer switch element 642, and a third layer switch element 624. The display user interface 233 can detect a selection of one of the one or more media interface elements or the multiple layers, such as using an optical sensor of the one or more display sensors 235 that detects a gesture by the user toward the one of the one or more media interface elements or the multiple layers.

The play/pause element 630, the fast forward element 632, the jump forward element 634, the jump reverse element 636, and the fast reverse element 638 can be selected by the user to control presentation of information by one or more of the multiple layers. The selection of the play/pause element 630 can cause one or more of the multiple layers to either play or pause a playback of information in the one or more of the multiple layers. The selection of the fast forward element 632 can cause one or more of the multiple layers to start a high speed playback (for example, ×1.5, ×2, ×3, ×5, ×10, ×25, or ×50 speed) of information in the one or more of the multiple layers. The selection of the jump forward element 634 can cause one or more of the multiple layers to skip a set period of time forward (for example, 10 seconds, 30 seconds, 1 minute, 5 minutes, 15 minutes, 30 minutes, or 1 hours) in playback of information in the one or more of the multiple layers. The selection of the jump reverse element 636 can cause one or more of the multiple layers to skip a set period of time backward (for example, 10 seconds, 30 seconds, 1 minute, 5 minutes, 15 minutes, 30 minutes, or 1 hours) in playback of information in the one or more of the multiple layers. The selection of the fast reverse element 638 can cause one or more of the multiple layers to start a high speed playback (for example, ×1.5, ×2, ×3, ×5, ×10, ×25, or ×50 speed) in reverse of information in the one or more of the multiple layers.

The play/pause element 630, the fast forward element 632, the jump forward element 634, the jump reverse element 636, and the fast reverse element 638 can operate on one or more of the multiple layers that may have been selected by the user prior to the selection of the play/pause element 630, the fast forward element 632, the jump forward element 634, the jump reverse element 636, or the fast reverse element 638. The play/pause element 630, the fast forward element 632, the jump forward element 634, the jump reverse element 636, and the fast reverse element 638 can thus assist the user with efficiently reviewing and understanding characteristics of the wound 412 and its neighboring area over time (such as over a period of seconds, minutes, hours, or days).

As shown in FIG. 6D, timestamps can be presented in augmented reality alongside the multiple layers. The first layer 610 can be presented alongside a timestamp of "2020 JAN 18 8:30 AM", which may indicate the information presented by the first layer 610 can correspond to the sensor data collected at the wound dressing 420 at Jan. 18, 2020, at 8:30 AM. The second layer 612 can be presented alongside a timestamp of "2020 JAN 18 8:30 AM", which may indicate the information presented by the second layer 612 can correspond to the sensor data collected at the wound dressing 420 at Jan. 18, 2020, at 8:30 AM. The first layer 610 and the second layer 612 may present sensor data collected at the wound dressing 420 at a common time. The third layer 614 can be presented alongside a timestamp of "2020 JAN 18 8:00 AM", which may indicate the information presented by the third layer 614 can correspond to the sensor data collected at the wound dressing 420 at Jan. 18, 2020, at 8:00 AM. The fourth layer 616 can be presented alongside a timestamp of "2020 JAN 18 7:00 AM", which may indicate the information presented by the fourth layer 616 can correspond to the sensor data collected at the wound dressing 420 at Jan. 18, 2020, at 7:00 AM. The third layer 614 and the fourth layer 616 may present sensor data collected at the wound dressing 420 at different times, as well as collected at different times from the common time for the first layer 610 and the second layer 612.

The first layer switch element 640, the second layer switch element 642, and the third layer switch element 624 can be selected by the user to switch positions of one or more of the multiple layers. The selection of the first layer switch element 640 can cause the first layer 610 and the second layer 612 to switch positions from the viewing perspective of the user. The selection of the second layer switch element 642 can cause the second layer 612 and the third layer 614 to switch positions from the viewing perspective of the user. The selection of the third layer switch element 644 can cause third layer 614 and the fourth layer 616 to switch positions from the viewing perspective of the user.

A less information element 650 can be presented in the wound treatment system 400 as illustrated in FIG. 6D. The more information element 650 can be presented in augmented reality by the display user interface 233, and the display user interface 233 can detect a selection of the less information element 650 by the user, such as using an optical sensor of the one or more display sensors 235 that detects a gesture by the user toward the less information element 650. The selection of the less information element 650 can remove the one or more media interface elements from presentation and trigger the wound treatment system 400 to appear as shown in FIG. 6B.

Computer System Components

Figure 7:
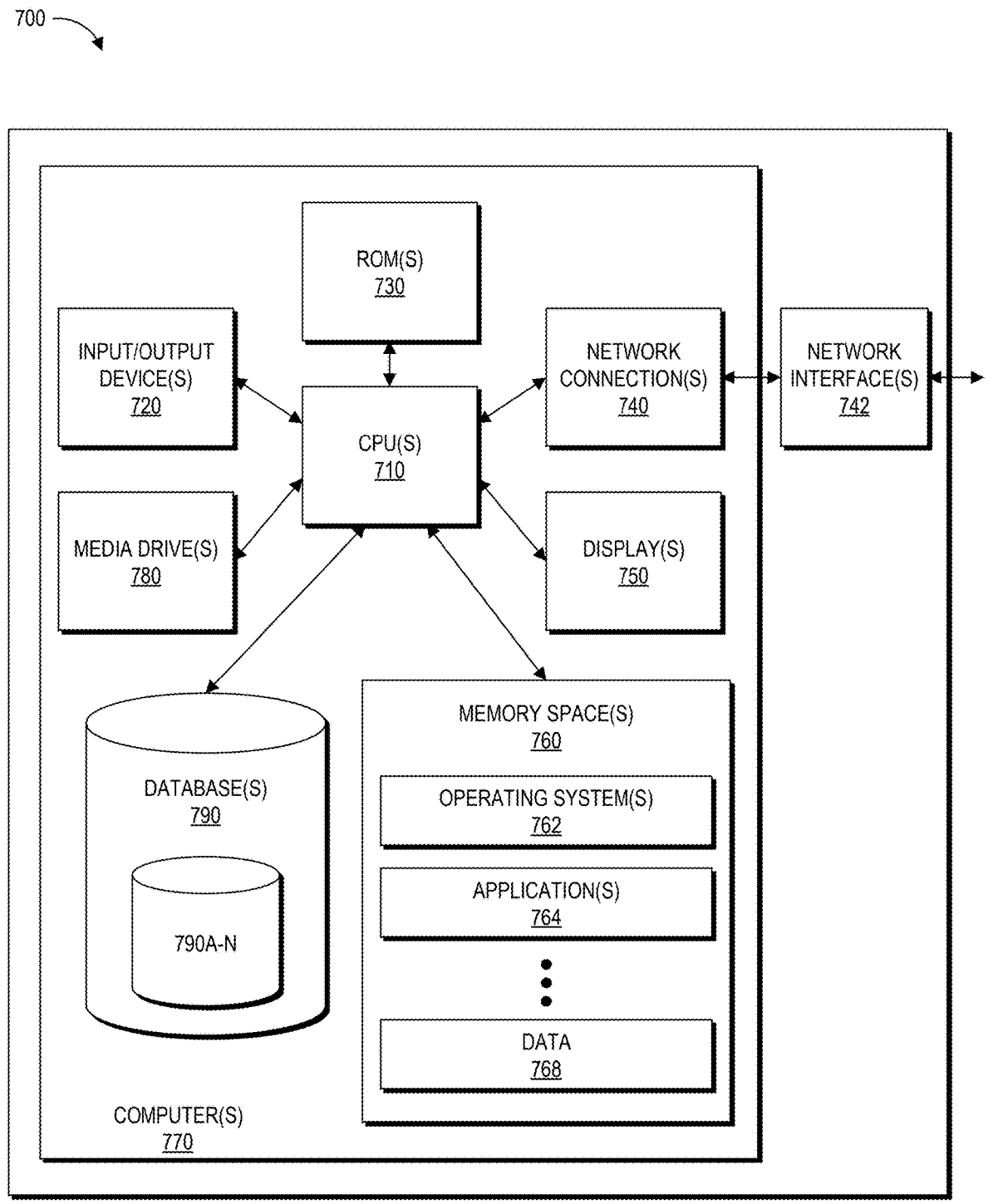
FIG. 7 illustrates a computer system.

FIG. 7 illustrates a computer system 700 usable to construct one or more of the devices (for instance, the monitor device 220 or the display device 230), systems, servers, or the like described or shown herein.

As shown in FIG. 7, the computer system 700 can include (i) a processor(s) (CPUs) 710, (ii) an input/output device(s) 720 configured to allow users to input and output information and interact with the computer system 700 as well as transfer and receive data or capture data with one or more sensors like an image sensor, (iii) a read only memory device(s) (ROMs) 730 or equivalents to provide nonvolatile storage of data or programs, (iv) a display(s) 750 such as a computer monitor or other display device, (v) a network connection(s) 740 and a network interface(s) 742 configured to allow the computer system 700 to connect to other systems, servers, or portable devices, as well as a memory space(s) 760 and a database(s) 790. The database(s) 790 may be further divided or distributed as sub-database(s) 790A-790N, with the sub-database(s) storing feature or function specific information associated with a particular feature or function. The various components shown in FIG. 7 may be incorporated in a computer(s) 770. It is noted that the various components shown in FIG. 7, including the database(s) 790, are typically included as part of the computer(s) 770, however, they may be external to the computer(s) 770 in some aspects. For example, the database(s) 790 may be external to the computer(s) 770 and may be part of a separate database computer system or networked database system. In some instances, the computer system 700 may be a computing device like a desktop computer, mobile phone, or a server.

The memory space(s) 760 may include DRAM, SRAM, FLASH, hard disk drives, or other memory storage devices, such as a media drive(s) 780, configured to store an operating system(s) 762, an application program(s) 764, and data 768, and the memory space(s) 760 may be shared with, distributed with or overlap with the memory storage capacity of the database(s) 790. In some aspects, the memory space(s) 760 may include the database(s) 790 or in some aspects the database(s) 790 may include the data 768 as shown in the memory space(s) 760. The data stored in the memory space(s) 760 or the database(s) 790 may include information, such as sensor data or data processing routines, or other types of data described herein.

Other Variations and Terminology

While certain approaches described herein utilize augmented reality, virtual reality can be used additionally or alternatively. While placement of a wound dressing is described as one application of the approaches described herein, the approaches can be applicable for different medical or non-medical uses. For example, the approaches described herein can be applicable for placing a measurement device, a wearable device, or the like.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines or computing systems that can function together.

One or more user inputs described in this disclosure may be received using one or more different mechanisms. For example, user interface controls may be selected by a user using one or more input options, such as a mouse, touch screen input, or keyboard input, among other user interface input options. The user interface controls selected by the user can include one or more of buttons, dropdown boxes, select boxes, text boxes, check boxes, slider controls, or other user interface controls.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, a microprocessor, a state machine, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A hardware processor can include electrical circuitry or digital logic circuitry configured to process computer-executable instructions. In another aspect, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain aspects include, while other aspects do not include, certain features, elements or states. Thus, such conditional language is not generally intended to imply that features, elements or states are in any way required for one or more aspects or that one or more aspects necessarily include logic for deciding, with or without author input or prompting, whether these features, elements or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A method of visualizing sensor data, the method comprising:
   determining a relative position of a wound dressing;
   generating one or more movement instructions from the relative position of the wound dressing, the one or more movement instructions being usable to guide placement by a user of the wound dressing on a wound of a patient;
   generating a placement outline indicating a region over the wound where the wound dressing should be placed;
   presenting the one or more movement instructions and the placement outline to the user via augmented reality so that the one or more movement instructions are overlaid on an area proximate to the patient from a viewing perspective of the user and the placement outline is overlaid on the wound, the one or more movement instructions and the placement outline facilitating covering the wound with the wound dressing;
   subsequent to the wound dressing being positioned on the wound, receiving sensor data generated by one or more sensors monitoring the wound;
   generating a graphical representation of the sensor data from the sensor data; and
   presenting the graphical representation of the sensor data to the user via augmented reality so that the graphical representation of the sensor data is overlaid on the area proximate to the patient from the viewing perspective of the user.

2. The method of claim 1, further comprising determining a location of a marking on or proximate to the wound dressing, wherein said presenting comprises presenting the graphical representation of the sensor data so that the graphical representation of the sensor data is positioned at a set distance from the location from the viewing perspective of the user.

3. The method of claim 1, wherein said presenting comprises presenting the graphical representation of the sensor data so that the graphical representation of the sensor data is positioned above the wound dressing from the viewing perspective of the user even as the user moves around the patient.

4. The method of claim 1, wherein the graphical representation of the sensor data comprises a color-coding of values of the sensor data.

5. The method of claim 1, wherein the graphical representation of the sensor data comprises a plurality of layers including a first layer representing first variations at the wound detected with a first type of sensor and a second layer representing second variations at the wound detected with a second type of sensor different from the first type of sensor, and said presenting comprises presenting the graphical representation of the sensor data so that the first layer and the second layer are separately displayed and overlaid on the area from the viewing perspective of the user.

6. The method of claim 5, wherein the first layer is positioned above the second layer from the viewing perspective of the user.

7. The method of claim 5, wherein the first variations comprise temperature variations, and the second variations comprise conductivity variations.

8. The method of claim 1, wherein the graphical representation of the sensor data comprises a first side and a second side opposite the first side, and the first side represents first sensor data detected on one side of the wound dressing and the second side represents second sensor data detected on another side of the wound dressing opposite the one side of the wound dressing, wherein said presenting comprises presenting the graphical representation of the sensor data so that, from the viewing perspective of the user, the first side is positioned above the one side of the wound dressing and the second side is positioned above the another side of the wound dressing.

9. The method of claim 1, wherein said receiving is performed in real-time with said presenting.

10. The method of claim 1, wherein said presenting comprises presenting the graphical representation of the sensor data on a head-mounted display.

11. The method of claim 1, further comprising generating the sensor data by the one or more sensors, wherein said generating the sensor data is performed in real-time with said presenting, and the one or more sensors are integrated in the wound dressing.

12. The method of claim 1, further comprising operating a negative pressure source fluidically connected to the wound dressing to provide negative pressure and deliver a negative pressure wound therapy to the wound.

13. The method of claim 1, further comprising:
   at a first time:
      presenting a first user interface control to the user via augmented reality;

detecting a user selection of the first user interface control; and responsive to detecting the user selection of the first user interface control, deactivating presentation of the graphical representation of the sensor data so that the graphical representation of the sensor data is no longer overlaid on the area proximate to the patient from the viewing perspective of the user; and at a second time:

presenting a second user interface control to the user via augmented reality;

detecting a user selection of the second user interface control; and responsive to detecting the user selection of the second user interface control, adjusting the graphical representation of the sensor data to illustrate changes in the sensor data over a period of time.

14. The method of claim 1, wherein the one or more movement instructions comprises a plurality of arrows each indicating a direction of movement of the wound dressing or a change in orientation of the wound dressing.

15. An apparatus for visualizing sensor data, the apparatus comprising:

an input interface configured to receive sensor data generated by one or more sensors configured to monitor a wound of a patient; and a controller configured to:

determine a relative position of a wound dressing;

generate one or more movement instructions from the relative position of the wound dressing, the one or more movement instructions being usable to guide placement by a user of the wound dressing on the wound;

generate a placement outline indicating a region over the wound where the wound dressing should be placed;

present the one or more movement instructions and the placement outline to the user via augmented reality so that the one or more movement instructions are overlaid on an area proximate to the patient from a viewing perspective of the user and the placement outline is overlaid on the wound, the one or more movement instructions and the placement outline facilitating covering the wound with the wound dressing;

subsequent to the wound dressing being positioned on the wound, generate a graphical representation of the sensor data from the sensor data received by the input interface; and output the graphical representation of the sensor data for presentation to a user via augmented reality so that the graphical representation of the sensor data is overlaid on the area proximate to the patient from the viewing perspective of the user.

16. The apparatus of claim 15, wherein the controller is configured to determine a location of a marking on or proximate to the wound dressing, and the controller is configured to output the graphical representation of the sensor data for presentation so that the graphical representation of the sensor data is positioned on a display at a set distance from the location from the viewing perspective of the user.

17. The apparatus of claim 15, wherein the controller is configured to output the graphical representation of the sensor data for presentation so that the graphical representation of the sensor data is positioned on a display above the wound dressing from the viewing perspective of the user.

18. The apparatus of claim 15, wherein the graphical representation of the sensor data comprises a plurality of layers including a first layer representing first variations at the wound detected with a first type of sensor and a second layer representing second variations at the wound detected with a second type of sensor different from the first type of sensor, and said presenting comprises presenting the graphical representation of the sensor data so that the first layer and the second layer are separately displayed and overlaid on the area from the viewing perspective of the user.

19. The apparatus of claim 15, wherein the graphical representation of the sensor data comprises a first side and a second side opposite the first side, and the first side represents first sensor data detected on one side of the wound dressing and the second side represents second sensor data detected on another side of the wound dressing opposite the one side of the wound dressing, wherein the controller is configured to output the graphical representation of the sensor data for presentation so that, from the viewing perspective of the user, the first side is positioned above the one side of the wound dressing and the second side is positioned above the another side of the wound dressing.

20. The apparatus of claim 15, further comprising:

a head-mounted display configured to present the graphical representation of the sensor data;

the one or more sensors, the one or more sensors being configured to generate the sensor data in real-time with the controller outputting the graphical representation of the sensor data for presentation; and the wound dressing, the one or more sensors being integrated in the wound dressing.

21. The apparatus of claim 15, wherein the controller is further configured to:

present a first user interface control to the user via augmented reality;

responsive to a user selection of the first user interface control, deactivate output of the graphical representation of the sensor data so that the graphical representation of the sensor data is no longer overlaid on the area proximate to the patient from the viewing perspective of the user;

present a second user interface control to the user via augmented reality; and responsive to a user selection of the second user interface control, adjust the graphical representation of the sensor data to illustrate changes in the sensor data over a period of time.

* * * * *